United States Patent
Lu et al.

(10) Patent No.: US 9,914,698 B2
(45) Date of Patent: Mar. 13, 2018

(54) STEAROYL AMINO ACID SALT AND PREPARATION METHOD AND APPLICATION THEREOF

(71) Applicant: Shanghai Jiaotong University School of Medicine, Huangpu District, Shanghai (CN)

(72) Inventors: Yang Lu, Shanghai (CN); Jianhua Liu, Shanghai (CN); Shuangqi Tang, Shanghai (CN); Hongzhuan Chen, Shanghai (CN)

(73) Assignee: SHANGHAI JIAOTONG UNIVERSITY SCHOOL OF MEDICINE, Huangpu District, Shanghai (CN)

( * ) Notice: Subject to any disclaimer, the term of this patent is extended or adjusted under 35 U.S.C. 154(b) by 0 days.

(21) Appl. No.: 15/110,228

(22) PCT Filed: Nov. 5, 2014

(86) PCT No.: PCT/CN2014/090381
§ 371 (c)(1),
(2) Date: Jul. 7, 2016

(87) PCT Pub. No.: WO2015/103901
PCT Pub. Date: Jul. 16, 2015

(65) Prior Publication Data
US 2016/0326096 A1    Nov. 10, 2016

(30) Foreign Application Priority Data

Jan. 8, 2014 (CN) .......................... 2014 1 0008341
Jul. 14, 2014 (CN) .......................... 2014 1 0334003

(51) Int. Cl.
*C07C 233/47* (2006.01)
*C07C 231/12* (2006.01)

(52) U.S. Cl.
CPC .......... *C07C 233/47* (2013.01); *C07C 231/12* (2013.01)

(58) Field of Classification Search
None
See application file for complete search history.

(56) References Cited

FOREIGN PATENT DOCUMENTS

CN           1974545    *  6/2007
CN        101240002 A     8/2008
(Continued)

OTHER PUBLICATIONS

Google Patents Machine Translation of CN 1974545, Jun. 2007.*
(Continued)

*Primary Examiner* — Karl J Puttlitz
(74) *Attorney, Agent, or Firm* — Panitch Schwarze Bellisario & Nadel LLP

(57) ABSTRACT

A stearoyl amino acid salt having a structural formula of the general formula (I), wherein $R_1$ is H or an aromatic base capable of being substituted by one or more substituents, or a $C_{1-4}$ straight chain or an alkyl with a branched chain, the substituent being an alcoholic hydroxyl group or a phenolic hydroxyl group; and $R_2$ is a $C_{11-25}$ saturated or unsaturated aliphatic group. Also provided are methods of preparing the stearoyl amino acid salt, and methods of using the stearoyl amino acid salt. Compared to a prototype drug stearoyl amino acid, the stearoyl amino acid salt described herein has excellent physicochemical properties, good stability, high relative bioavailability, a strong drug effect and a high safety factor. It is thus expected to become a candidate for clinical treatment of neurodegenerative diseases and acute brain injury, and a clinical drug for weight loss, thus having broad application prospects.

(Continued)

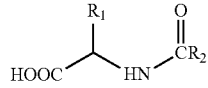

(I)

10 Claims, 13 Drawing Sheets

(56) References Cited

FOREIGN PATENT DOCUMENTS

| CN | 101674852 A | 3/2010 |
|---|---|---|
| CN | 101743242 A | 6/2010 |
| CN | 103980148 A | 8/2014 |

OTHER PUBLICATIONS

Database CAPLUS Chemical Abstracts Service, Columbus, Ohio, US; Database Accession No. 105:173027, Abstract of Medal, Acta Chemica Scandinavica, Series B: Organic Chemistry and Biochemistry, (1986), B40(4), 242-9.*

Int'l Search Report issued Feb. 27, 2015 in Int'l Application No. PCT/CN2014/090381.

Guo, "Biochemical Mechanism of Endocannabinoid System in Type 2 Diabetes and Obesity", Chinese Journ. of Geriatric Care, vol. 6. No. 6, 4 pgs. (Dec. 2008).

Yang, "Protective Effects of N-Stearoyltyrosine on Caspase-Independent Cell Death and Their Mechanism", Doctoral Dissertations of Shanghai Jiaotong University, 10 pgs. (May 2013).

Written Opinion issued Feb. 27, 2015 in Int'l Application No. PCT/CN2014/090381 (English Translation).

\* cited by examiner

STEAROYL AMINO ACID SALT AND PREPARATION METHOD AND APPLICATION THEREOF

CROSS-REFERENCE TO RELATED APPLICATION

This application is a Section 371 of International Application No. PCT/CN2014/090381, filed Nov. 5, 2014, which was published in the Chinese language on Jul. 16, 2015, under International Publication No. WO 2015/103901A1, and the disclosure of which is incorporated herein by reference.

FIELD OF THE INVENTION

The present invention relates to medicine technology, in particular, to a stearoyl amino acid salt and preparation method and application thereof.

BACKGROUND OF THE INVENTION

Cerebrovascular diseases are common and frequently-occurring. They present a huge threat to human health due to their high fatality, disability, and resulting medical expenses; and patients affected tend to be increasingly younger. Ischemic brain injury is a common brain disease due to blood circulation disorder. Cerebral ischemia may cause energy metabolism dysfunction in local brain tissues, excitatory amino acid cytotoxic, excessive calcium influx, inflammatory cytokine release, free radical damage and other malignant cascade reactions, eventually leading to neuronal death. Currently, there are a variety of neuroprotective drugs for ischemic brain injury, including glutamate receptor antagonist, glutamate release inhibitors, antioxidants, calcium ion chelating agent, etc. Pathologically, however, ischemic brain injury involves a cascade process including multiple factors and channels; it is difficult for drugs with a single mechanism alone to effectively inhibit such a complex process. Hence unsatisfactory clinical treatment. Clinically, more effective drugs against ischemic brain injury are in great need.

Endocannabinoids system (ECS) acts as a protector by participating in regulating oxidative stress, trauma, ischemia and other pathological processes. ECS has become a new target for use of neuroprotective drugs. ECS is activated after ischemic injury; postsynaptic neurons are synthesized on demand and a large number of endocannabinoids anandamide (AEA) are released, acting on the presynaptic neurons cannabinoid receptors; and a variety of dysfunctions of damaged neurons are regulated through negative feedback to protect damaged nerve cells.

The N-stearoyl amino acid (e.g. N-stearoyl tyrosine, NsTyr) developed by our laboratory is a new AEA analogue, protecting nerve by intervening in ECS metabolic process. Previous studies have confirmed that NsTyr significantly intervened in vitro slices, neurons and a variety of PC12 cell injuries, improved the survival rate of hippocampal CA1 pyramidal cells for gerbil model in acute ischemia injury, and lessened the apoptosis of ischemic damaged neurons. However, N-stearoyl amino acid had a low solubility in water, and a low bioavailability as a neuroprotective drug.

Previous research of stearoyl amino acid and any salt as such focused on the nerve protective function of this compound. So far there has been no report of stearoyl amino acid or the medicinal salt thereof as a weight-loss drug. However, obesity is the leading cause to diabetes, cardiovascular diseases and nonalcoholic fatty liver diseases. What's worse, adult obesity rate has been sharply rising year by year worldwide, say, by 22% in 2013. Appetite suppressants sibutramine and rimonabant, though effective in weight loss, had to drop out of the market due to their side effects such as depression. FDA-approved weight-reducing drug Orlistat was reported to give a rare case of liver damage in phase IV clinical monitoring. Therefore, considering complex causes to obesity, desired weight loss drugs should have good security and be able to speed up hydrolysis against fat absorption and synthesis by regulating metabolic pathways within the body. By now, research of drugs for obesity has focused on discovering natural products that promote β-oxidation (the chief way of fat hydrolysis and catabolism). However, such natural products seldom reach desired effects when applied to fat animal models; at the same time, results of security assessment have also limited their development. Thus, developing new weight-reducing drugs with different mechanism meets huge societal demand, and theoretically is of great significance as well.

SUMMARY OF THE INVENTION

The technical problem that the present invention attempts to solve is to provide a stearoyl amino acid salt. Compared with prototype drug stearoyl amino acid, the stearoyl amino acid salt described herein has better physicochemical properties, stability, and a significantly higher relative bioavailability.

In addition, a method of preparation and application thereof is also needed to provide for the stearoyl amino acid salt described for this purpose.

To solve the aforesaid technical problems, the present invention aims to take the following technical schemes:

In one aspect the present invention provides a stearoyl amino acid salt, wherein the stearoyl amino acid described herein has a structural formula of the following general formula (I):

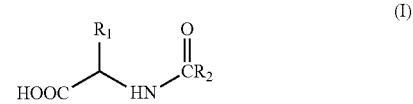

wherein $R_1$ indicates H or an aromatic base capable of being substituted by one or more substituents, or $C_{1-4}$ straight chains or alkyl with a branched chain, the substituent being an alcoholic hydroxyl group or a phenolic hydroxyl group; and $R_2$ indicates $C_{11-25}$ saturated or unsaturated aliphatic groups.

The above $C_{1-4}$ alkyl is a straight chain or branched chain alkyl with 1~4 carbon atoms, e.g. methyl, ethyl, propyl, isopropyl, butyl, isobutyl, tertiary butyl, sec-butyl, preferably an alkyl with 1~2 carbon atoms.

The above $C_{11-25}$ aliphatic group is a saturated or unsaturated aliphatic group with 11~25 carbons, wherein the saturated aliphatic group refers to a straight chain or branched chain alkyl and naphthenic group, e.g. dodecyl, octadecyl, cyclododecyl, cyclooctadecyl; and the unsaturated aliphatic group refers to alkenyl (e.g. 1-dodecenyl, 2-dodecenyl), alkynyl (e.g. 1-octadecynyl, 2-octadecynyl) or chain dienyl (e.g. 1,3-octadecenyl, 7,9-octadecenyl), preferably straight chain or branched chain alkyls with 17~25 carbon atoms, and most preferably straight chain alkyls with 17 carbon atoms.

Preferably, the stearoyl amino acid salt described herein has a structural formula of the following formula (II) or formula (III):

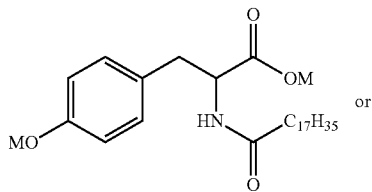

(II)

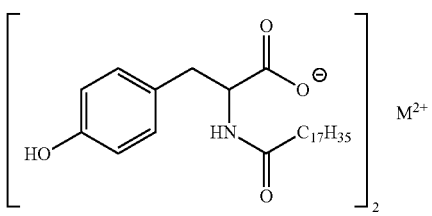

(III)

wherein M in the formula (II) is mono-valent metal cation or $NH_4^+$; and M in the formula (III) is divalent metal cation.

Preferably, M in the formula (II) is selected from $K^+$, $Na^+$, or $NH_4^+$.

Preferably, M in the formula (III) is selected from $Ba^{2+}$, $Ca^{2+}$, or $Mg^{2+}$.

In another aspect the present invention provides a method for preparing stearoyl amino acid salt. The method includes: preparing the stearoyl amino acid salt from N-stearoyl amino acid methyl ester in the following formula (VII) through alkaline hydrolysis.

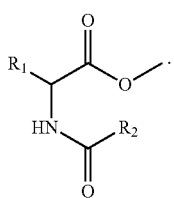

(VII)

Preferably, N-stearoyl amino acid methyl ester in the formula (VII) is prepared through treating the compounds of the following formula (VI)

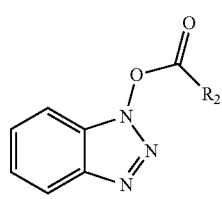

(VI)

with the compounds of the following formula (V) under alkaline conditions.

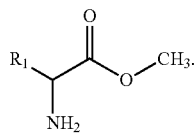

(V)

Preferably, the compounds of the formula (VI) are prepared through treating the following formula (IV) compounds and coupling agent 1-benzotriazole hydroxyl groups;

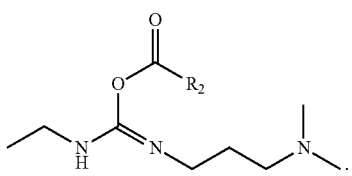

(IV)

Preferably, the formula (IV) compounds are prepared by reacting 1-ethyl-(3-dimethyl amino propyl) carbonyl imine hydrochloride, stearic acid and triethylamine with catalyst 4-dimethyl amino pyridine.

In another aspect the present invention also provides a pharmaceutical composition, containing a safe and effective amount of the stearoyl amino acid salt described and a pharmaceutically acceptable carrier.

In another aspect the present invention provides a pharmaceutical composition for cerebral ischemia, stroke, Alzheimer's or Parkinson's diseases, containing a safe and effective amount of the stearoyl amino acid salt described and a pharmaceutically acceptable carrier.

In another aspect the present invention provides a pharmaceutical composition for weight loss, containing a safe and effective amount of the stearoyl amino acid or any medicinal salt as such, and a pharmaceutical acceptable carrier.

In another aspect the present invention provides a pharmaceutical composition for fatty liver, containing a safe and effective amount of the stearoyl amino acid or any medicinal salt as such, and a pharmaceutical acceptable carrier.

The above acceptable carriers are non-toxic, and can be applied as a helper, and no hostile consequences have occurred upon the treatment effects of stearoyl amino acid salt. Such carriers may be available to any skilled personnel in the art, including solid, liquid, quasi-solid excipients or gas excipients in aerosol compositions. Such solid drug excipients include starch, cellulose, talc, glucose, lactose, sucrose, gelatin, malt, rice, flour, chalk, silica, magnesium stearate, stearic acid, glycerin stearoyl ester, sodium chloride, anhydrous skim milk. Liquid and quasi-solid excipients, which can be selected from glycerol, propylene glycol, water, ethanol and a variety of oils, include those from petroleum, animals, plants or from man-synthesis, e.g. peanut oil, soybean oil, mineral oil, and sesame oil. Preferable liquid carriers, particularly when used for injectable solutions, include water, saline, glucose aqueous solution and glycol. Other auxiliary agents such as flavorings and sweeteners can be added to the composition as well.

The stearoyl amino acid salt of the present invention is administered with an effective dose for treatment orally, wholly (e.g. transdermal, intranasal or by means of suppository) or parenterallly (e.g. intramuscular, intravenous or subcutaneous), preferably orally, which allows regulation depending on disease activity.

The actual application dose of stearoyl amino acid salt of the present invention (i.e. active ingredients) depends on multiple factors, including the severity of illness, the age and health of recipients, the efficiency of compounds used, application approaches and forms, etc.

The dosage forms of pharmaceutical compositions of the present invention can be prepared by conventional pharmaceutical means, for instance, mixing the stearoyl amino acid salt (active ingredients) with one or more carriers, then making them into required dosage forms, e.g. tablets, pills, capsules, semi-solids, powder, sustained-release dosage form, solution, suspension, auxiliary dosage, aerosol, etc.

In another aspect the present invention provides the application of the stearoyl amino acid salt in preparation of neuroprotective drugs, including those for cerebral ischemia, stroke, Alzheimer's or Parkinson's diseases.

In another aspect the present invention provides the application of the stearoyl amino acid salt in preparation of drugs for weight loss.

In another aspect the present invention provides the application of the stearoyl amino acid salt in preparation of drugs for fatty liver.

Compared with prototype drug stearoyl amino acid, the stearoyl amino acid salt of the present invention has better physicochemical properties, stability, storability, higher relative bioavailability, stronger drug effects, a bigger therapeutic window, and a higher safety factor. On the ischemia-reperfusion model, the stearoyl amino acid salt significantly shrank cerebellar infarction area, lessened ischemia-caused brain edema and nerve injury; significantly improved the nerve defect functional scores of experimental animals as well as animal spatial learning and memory abilities. Results of test on Alzheimer's disease mouse model show that the stearoyl amino acid salt obviously improved the symptoms of Alzheimer's disease. Results of preclinical pharmacokinetic tests on KM mice by oral administration show that the stearoyl amino acid or its medicinal salt could significantly reduce the weight of obese mice, and high safety as well. Therefore, the stearoyl amino acid salt of the present invention is likely to become not only a candidate for clinical treatment of neurodegenerative diseases and acute brain injury, but also a drug for clinical weight-reducing, foretelling broad application prospects.

BRIEF DESCRIPTION OF THE DRAWINGS

The following is a further detailed description of the present invention with figures and specific embodiments.

In FIGS. 16~21. ND, standard diet blank control group; HFD I, high-fat feed blank control group; HFD II, low-dose NST-2K group (20 mg/kg/day); HFD III, medium-dose NST-2K group (60 mg/kg/day); HFD IV, high-dose NST-2K group (100 mg/kg/day); HFD V, positive control group (100 mg/kg/day Orlistat).

DETAILED DESCRIPTION OF THE INVENTION

EXAMPLE 1

Active Ester Method N-Stearoyl Amino Acid

Figure 1:
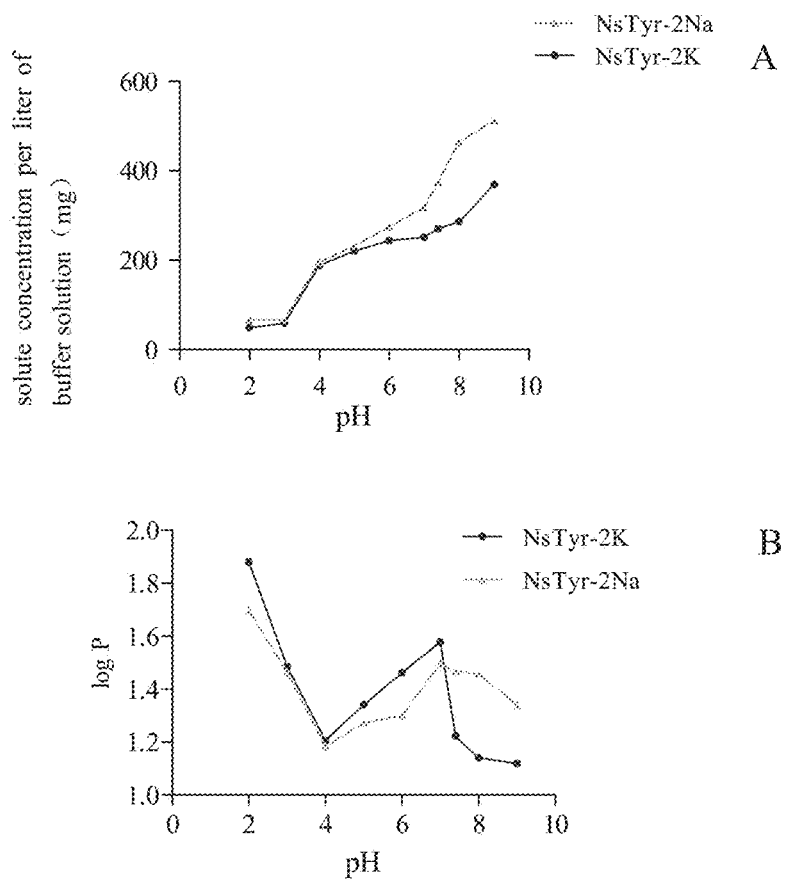
FIG. 1 shows equilibrium solubility curve and apparent lipid-water distribution coefficient curve in Embodiment 4 of the present invention.

In this embodiment active ester method was used to prepare N-stearoyl amino acid, which made the process a batch production, well-suited to industrial application. The following is a detailed description of reaction steps of active ester method, taking preparation of N-stearoyl tyrosine (NsTyr) as an example.

1. Complete Reaction Steps of Preparing NsTyr by Active Ester Method

As shown in the following reaction steps, the active ester method used N,N-dicyclohexyl carbon imide (DCC) and N-hydroxy succinimide (NHS), and NHS reacted with stearic acid under the effect of dehydrating agent DCC to produce active ester and then directly reacted with L-tyrosine to produce NsTyr, wherein THF was tetrahydrofuran.

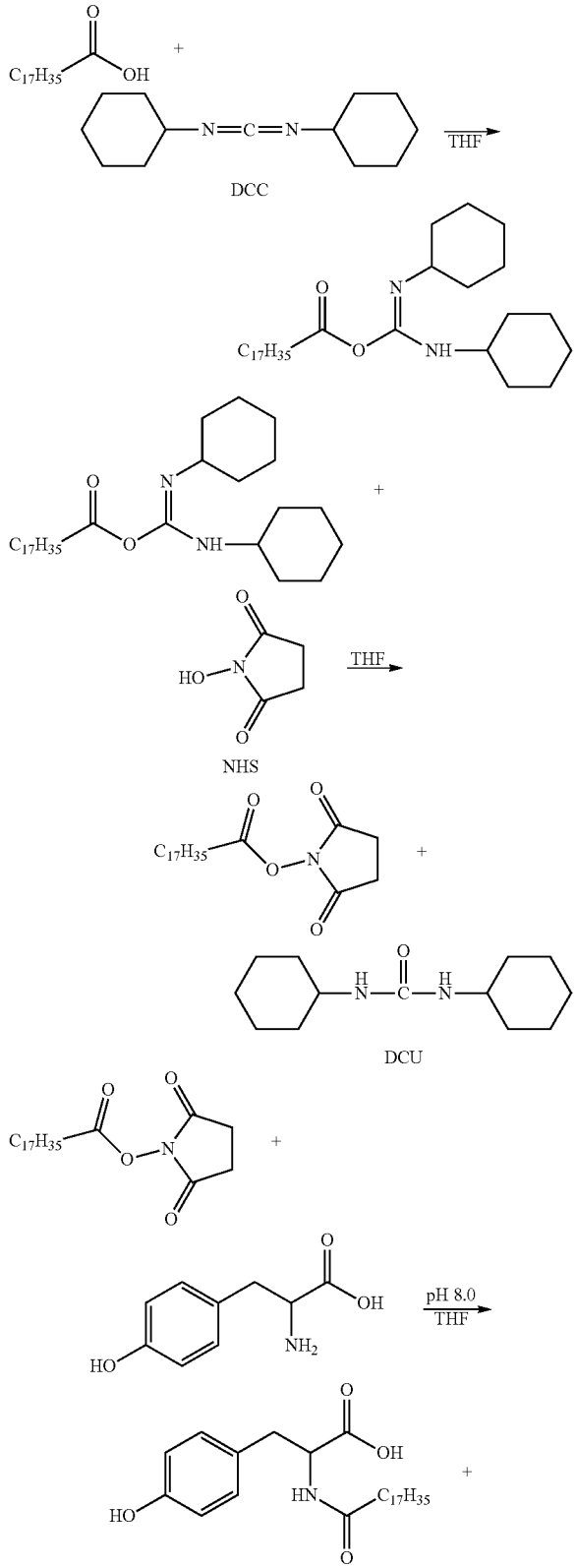

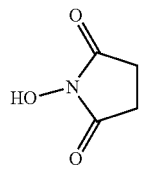

2. Preparation of Intermediate NHS Stearic Acid Ester

To a 1.000-ml round-bottom flask was added 100 g (352 mmol) of stearic acid, 60 g (521 mmol) of N-hydroxy succinimide and 800 ml of anhydrous THF. After being dissolved and ice-bath stirred, 90 g (436 mmol) of DCC was added. After 2 h stirring, the reaction continued for additional 12 h at room temperature. White solid by-product N,N-dicyclohexyl urea (DCU) was filtered off. After the resulting filtrate was evaporated to dryness, coarse products were obtained and were recrystallized with methanol at room temperature. Then 76.2 g of silver-white flake-like crystallized intermediates was obtained, with a yield of 83.6%, and m.p. 76-79° C.

3. Preparation of NsTyr

To a white 5,000-ml round-bottom flask was added 100 g (550 mmol) of L-tyrosine, 265 g (2,500 mmol) of sodium bicarbonate, and 2,000 ml of distilled water. After being heated to dissolve, 1,000 ml of THF solution containing 100 g (262 mmol) of intermediates was added while stirring at room temperature. After TLC confirmed that the reaction had been completed, insolubles were filtered off, and the pressure of filtrate was reduced and THF was removed by evaporation. To the concentrate was added 1,000 ml of distilled water, and the pH value was adjusted to 1 with 1 mol/L HCL solution, and white solids were precipitated. To this suspension was added thermal ethyl acetate (500 ml per times). After solids dissolved, the acetic acid and ethyl ester phase were extracted. The above operation was repeated again, and the organic phases were combined. Washing was done once with saturated salt water (1,000 ml), and drying was done with anhydrous sodium sulfate. Then filtration and drying gave white coarse products from the filtrate. The coarse products were treated with methanol/acetone and recrystallized at room temperature, and 74.3 g of white solid was obtained, with a yield of 62.1%, and m.p. 100-103.4° C.

EXAMPLE 2

Preparation of N-Stearoyl Amino Acid by One-Pot Method

In this embodiment one-pot method was used to prepare N-stearoyl amino acid. This method requires only mild reaction conditions, without having to be limited by amino acid solubility and system pH, yet with a desired yield and purity. The following is a detailed description of reaction steps of one-pot method, taking preparation of NsTyr by one-pot method as an example.

1. Complete Reaction Steps for Preparing NsTyr Methyl Ester by One-Pot Method

At room temperature, 1-ethyl-(3-dimethyl amino propyl) carbodiimide hydrochloride reacted with pre-synthesized L-tyrosine methyl ester in alkaline conditions with 1-hydroxy benzotriazole HOBT as coupling agent, 4-dimethyl aminopyridine DMAP as catalyst by one-pot method to synthesize NsTyr methyl ester.

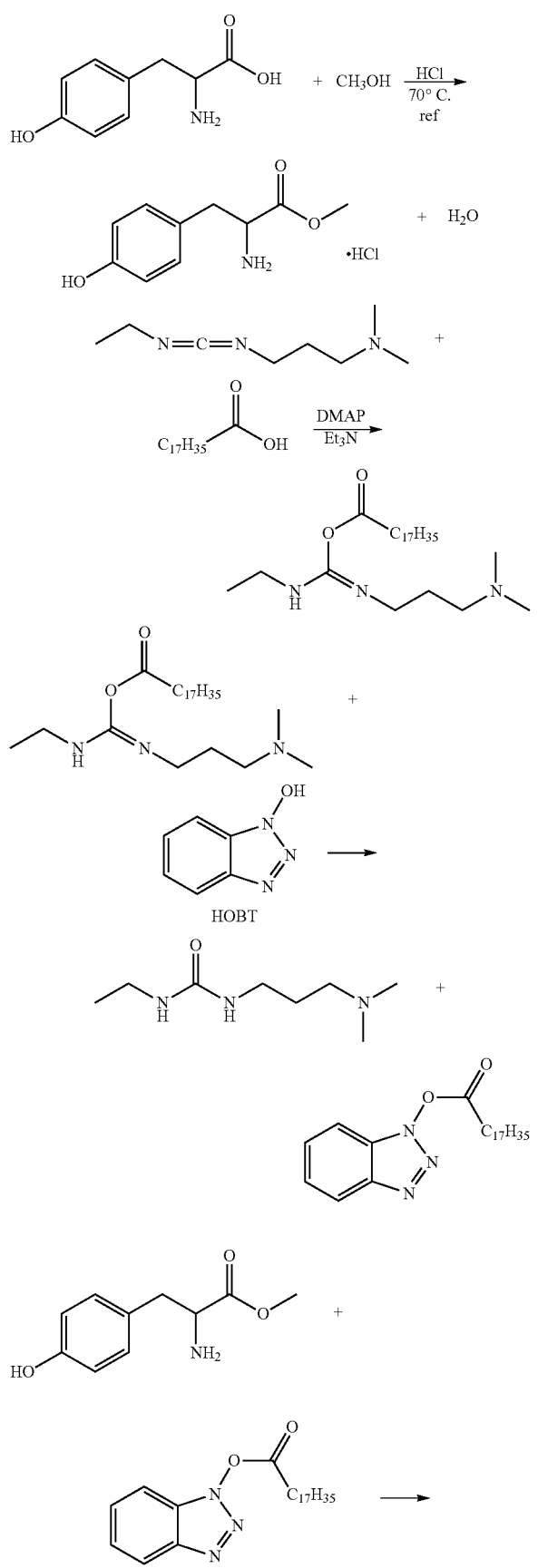

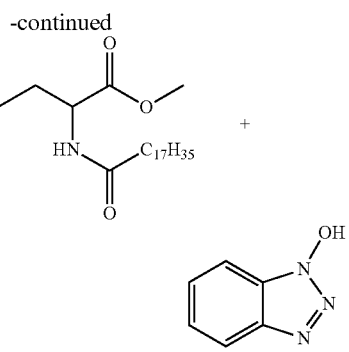

2. Preparation of Tyrosine Methyl Ester

To a 25-ml bottle with two necks, one of which was connected to a drying tube and the other of which was connected to a dropping funnel, was add 5 ml of anhydrous methanol. Then 0.8 ml of acetyl chloride ice was dropwise added under ice-bath salt conditions. After 30-min stirring, hydrochloric acid methanol was obtained. To an additional 100-ml round-bottom flask was added 0.905 g of L-tyrosine, and 5 ml of methanol. Then hydrochloric acid methanol was added while stirring until the solution became clear, and was refluxed 24 h. The reaction liquid anhydrous sodium sulfate was dried and filtrated, and yellow flake-like crystallized L-tyrosine methyl ester hydrochloride was obtained after the solvent was evaporated from the filtrate. To this solid was added saturated sodium bicarbonate solution (20 ml) until bubbles no longer came out, and extraction was made twice with methylene chloride (30 ml). Then the organic phase was dried, and evaporated to dryness, and 1.07 g of yellow solid L-tyrosine methyl was produced, with a yield of 95.6%.

3. NsTyr Methyl Ester (by One-Pot Method)

To a 250-ml round-bottom flask were added 1.704 g (6 mmol) of stearic acid, 1.22 ml (9.8 mmol) of triethylamine, 0.920 g (4.8 mmol) of 1-ethyl-(3-dimethyl amino propyl) carbonyl two imine hydrochloride, 0.029 g (0.24 mmol) of 4-dimethyl amine pyridine (DMAP), 0.648 g (4.8 mmol) of 1-hydroxy benzotriazole (HOBT), 1.11 g (4.8 mmol) of L-trosine methyl, and 80 ml of methylene chloride. Stirring was done at room temperature for 24 h, with TLC monitoring. To the coarse products was added 1 mol/L HCL solution for washing until no white floc appeared. Extraction was made three times with dichloromethane. The organic phases were combined. To the above collected organic phase was added saturated sodium bicarbonate solution for washing until no bubbles came out. Again, extraction was made three times with dichloromethane, and the organic phases were combined. The above collected dichloromethane phase was washed with saturated salt solution. After anhydrous sodium sulfate was dried and concentrated, 1.4 g of coarse product was obtained. By silica gel column chromatography, 588.6 mg of white powder L-NsTlr methyl ester was obtained from developing solvent dichloromethane/methanol (4/1), with a yield of 82.7%, and m.p. 100-104° C.

To the products was added 10 ml of 1 mol/L potassium hydroxide methanol solution. When at 70° C. reflux remained three hours, then the clarified liquid kept refrigerated for 24 h at 4° C. After filtering, a coarse product was obtained and was washed two or three times with acetone elution. After drying, 608.1 mg of white solid NsTyr-2K was obtained, with a yield of 95.6%.

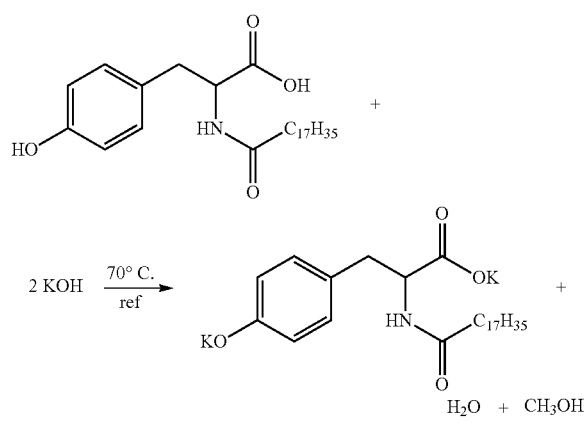

EXAMPLE 3

Preparation of N-Embodiment 3 Stearoyl Amino Acid Salt

1. Preparation of N-stearoyl tyrosine potassium salt, sodium salt, ammonium salt To a 250-ml round-bottom flask was added 40 ml of 1 mol/L ammonia, 60 ml of water to dissolve. Then 16 g (36 mmol) of NsTyr was added while stirring. The solution became clear when heated to 60° C. The solution kept refrigerated for 72 h at 4° C. After filtering, light yellow solids were obtained, and sprayed with acetone elution two or three times. After drying, 10.7 g of white powdery solid NsTyr-2NH$_4$ was obtained, with a yield of 62.3%.

Using the above method, with 5 g (125 mmol) of sodium hydroxide to substitute 40 ml of 1 mol/L ammonia, 15.7 g of white powder solid NsTyr-2Na was obtained, with a yield of 89.4%.

Using the above method, with 5 g (89 mmol) potassium hydroxide to substitute 40 ml of 1 mol/L ammonia, 17.9 g of white powdery solid NsTyr-2K was obtained, with a yield of 95.6%.

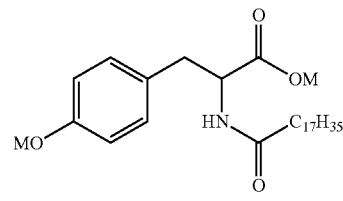

M = NH$_4$, K, Na

2. Preparation of N-Stearoyl Tyrosine Barium Salt, Magnesium Salt, Calcium Salt

To a 250-ml round-bottom flask was added 60 ml of aqueous solution containing 16 g (92 mmol) of barium hydroxide. Then 16 g (36 mmol) of NsTyr was added while stirring. The solution became clear when heated to 80° C. The solution kept refrigerated for 72 h at 4° C. After filtering, deep yellow solids were obtained, and sprayed with acetone elution two or three times. After drying, 15.4 g of white granular solid (NsTyr)$_2$Ba was obtained, with a yield of 83.6%.

Using the above methods, with 10 g (119 mmol) of magnesium carbonate to substitute 16 g (92 mmlol) of barium hydroxide, 11.9 g of white granular solid NsTyr$_2$Mg, with a yield of 72.6%.

Using the above methods, with 10 g (100 mmol) of calcium carbonate to substitute 16 g (92 mmlol) of barium hydroxide, 12.8 g of white granular solid NsTyr$_2$Ca was obtained, with a yield of 76.7%.

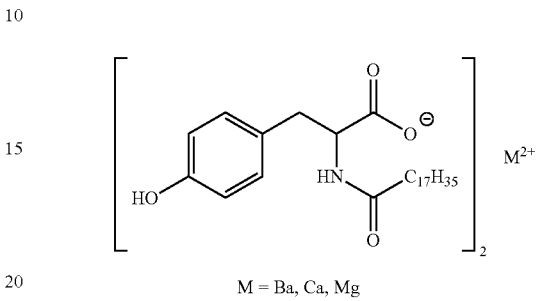

M = Ba, Ca, Mg

EXAMPLE 4

Test of N-Stearoyl Amino Acid Salt Physicochemical Constants and Pharmacokinetic Parameters 1. Equilibrium Solubility and Apparent Lipid-Water Distribution Coefficient The shake-flask method was used to test the equilibrium solubility of NsTyr, NsTyr-2K, NsTyr-2Na in water at 37° C. The solubility of NsTyr was below 100 mg/100 ml water, and that of NsTyr-2K, NsTyr-2Na was respectively 513.704 mg/100 ml water, and 926.551 mg/100 ml water. The apparent lipid-water distribution coefficient log p of NsTyr-2K, NsTyr-2Na was respectively 1.512 and 1.477. Under different pHs, see Table 1 for the equilibrium solubility test data of NsTyr-2K, NsTyr-2Na; and see Table 2 for the apparent lipid-water distribution coefficient of NsTyr-2K and NsTyr-2Na. And the equilibrium solubility curve and the apparent lipid-water distribution coefficient curve are shown in FIG. 1.

TABLE 1

Equilibrium solubility of NsTyr-2K and NsTyr-2Na in buffer solutions under different pHs

| pH | NsTyr-2K (mg/L) | NsTyr-2Na (mg/L) |
|---|---|---|
| 2.0 | 49.290 | 66.938 |
| 3.0 | 58.504 | 66.334 |
| 4.0 | 188.155 | 195.371 |
| 5.0 | 220.693 | 232.102 |
| 6.0 | 243.482 | 274.629 |
| 7.0 | 251.430 | 318.016 |
| 7.4 | 270.414 | 374.484 |
| 8.0 | 285.935 | 463.902 |
| 9.0 | 369.807 | 512.644 |

TABLE 2

Apparent lipid-water distribution coefficient of NsTyr-2K and NsTyr-2Na in buffer solutions under different pHs

| pH | NsTyr-2K Ko/w | LogP | NsTyr-2Na Ko/w | LogP |
|---|---|---|---|---|
| 2.0 | 76.020 | 1.881 | 49.913 | 1.698 |
| 3.0 | 30.571 | 1.485 | 28.980 | 1.462 |
| 4.0 | 16.020 | 1.205 | 15.224 | 1.183 |
| 5.0 | 21.934 | 1.341 | 18.710 | 1.272 |
| 6.0 | 28.935 | 1.461 | 19.963 | 1.300 |
| 7.0 | 37.855 | 1.578 | 31.436 | 1.497 |
| 7.4 | 16.674 | 1.222 | 29.286 | 1.467 |
| 8.0 | 13.797 | 1.140 | 28.704 | 1.458 |
| 9.0 | 13.140 | 1.119 | 21.872 | 1.340 |

The data of equilibrium solubility and apparent lipid-water distribution coefficient in the above Tables 1 and 2 and FIG. 1 show that low endogastric pH reduced a lot of NsTyr-2K and NsTyr-2Na into existence as prototype drugs, exerting effects through biological membrane absorption. After entering the intestine, the equilibrium solubility increased sharply, and the apparent lipid-water distribution coefficient plummeted; the drugs mainly existed in the form of ions, thus having difficulty to enter into blood through biological membrane absorption. Compared with prototype drugs, both NsTyr-2K and NsTyr-2Na had a significantly enhanced solubility.

2. Stability Assessment

Considering that prototype drug stearoyl amino acid tend to absorb moisture, cake and become yellowish during long-term storage, the stearoyl amino acid is now converted into a form of active salt thereof. And the stability of NsTyr-2K and NsTyr-2Na was tested as required for bulk pharmaceutical chemicals according to the *People's Republic of China Pharmacopoeia* 2010. Related influencing factors (high temperature, high humidity and strong light) test, acceleration test and long-term test showed that NsTyr-2K and NsTyr-2Na have stable properties, with a difference of less than 5°% in items involved (appearance, weight gain, melting point and purity) differences, having met the standards of the Pharmacopoeia. Thus NsTyr-2K is superior to the prototype drug thereof in terms of stability.

3. Absorption Kinetics Data

Figure 2:
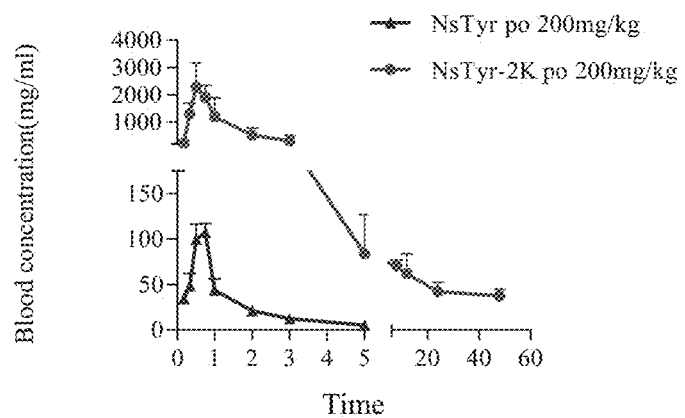
FIG. 2 shows blood concentration-time curve after rats were orally fed with NsTyr-2K and NsTyr in Embodiment 4 of the present invention.

Ten SD rats weighing 150-180 g were randomly divided into two groups, each comprising five, with males and females combined. After intragastric administration of 200 mg/kg of saline solution containing NsTyr and NsTyr-2K, the average blood concentration-time curve thereof was respectively shown in FIG. 2. The metabolic kinetic parameters for SD rats after oral administration of 200 mg/kg of NsTyr and NsTyr-2K are shown in Table 3.

TABLE 3

The metabolic kinetic parameters for SD rats after oral administration of 200 mg/kg of NsTyr and NsTyr-2K

| Parameter | NsTyr | NsTyr-2K |
|---|---|---|
| AUClast (h * g/ml) | 0.13 | 3.49 |
| AUCinf (h * g/ml) | 0.14 | 3.69 |
| MRTlast (h) | 1.38 | 2.19 |
| T1/2 (h) | 1.49 | 2.90 |
| Tmax (h) | 0.75 | 0.60 |
| Cmax (g/ml) | 0.11 | 2.40 |

The above comparison of metabolic kinetic parameters shows that, compared with NsTyr, NsTyr-2K had an area lying under the curve AUC multiplied by 30 times, with a significantly enhanced relative bioavailability, and an obviously prolonged half-life period (nearly doubled); that a surge of peak concentration Cmax (approximately multiplied by 20 times) and a sharp drop of the time to peak Tmax mean that NsTyr-2K absorption rate in the body was big, and the dosage of administration might be appropriately reduced to decrease the possibilities of toxicity reaction and increase therapeutic window and safety factor. In view of dosage forms, NsTyr limited by solubility, existed in the form of suspension; NsTyr-2K salts with high solubility could be prepared and delivered into homogeneous solutions.

EXAMPLE 5

Protection of N-Stearoyl Amino Acid Salt Against Neurobehavioral Disorder Caused by Cerebral Ischemia Reperfusion Injury Taking N-stearoyl amino acid potassium NsTyr-2K as an example, a gerbil model with global ischemia reperfusion injury was used to assess the protective role of NsTyr-2K against neurobehavioral disorder caused by cerebral ischemia-reperfusion injury by examining the changing behavioral indexes such as spatial, learning and cognitive functions in the perspective of overall animals during passive dark avoidance test and Morris water maze test.

1. Neurobehavioral Scores of Acute Cerebral Ischemia Reperfusion Model

Figure 3:
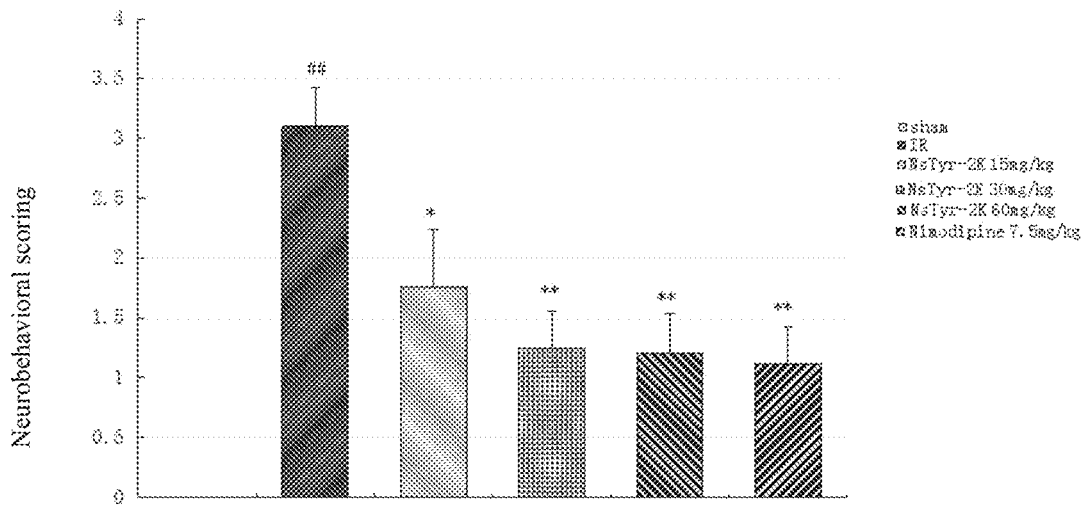
FIG. 3 shows NsTyr-2K neurobehavioral scoring results in Embodiment 5 of the present invention.

As shown in FIG. 3, neurobehavioral scores show that no case of ischemic symptoms was found in the sham operation group (the normal group), thus scoring 0. Compared with the sham operation group (the normal group), the ischemic model group showed obvious nerve dysfunction, scoring 3.1+/−0.32 (P<0.01), neurologically much higher than the sham operation group. Compared with the ischemia model group, three-dose groups of 15, 30, 60 mg/kgs of NsTyr-2K showed progressively reduced symptoms of ischemia-induced nerve injury, respectively 1.76+/−0.48, 1.25+/−0.31 and 1.21 0.33, suggestive of a dose-effect connection; and the corresponding figure was 1.12+/−0.31 for the nimotop (the positive control group).

2. Dark Avoidance Test

Figure 4:
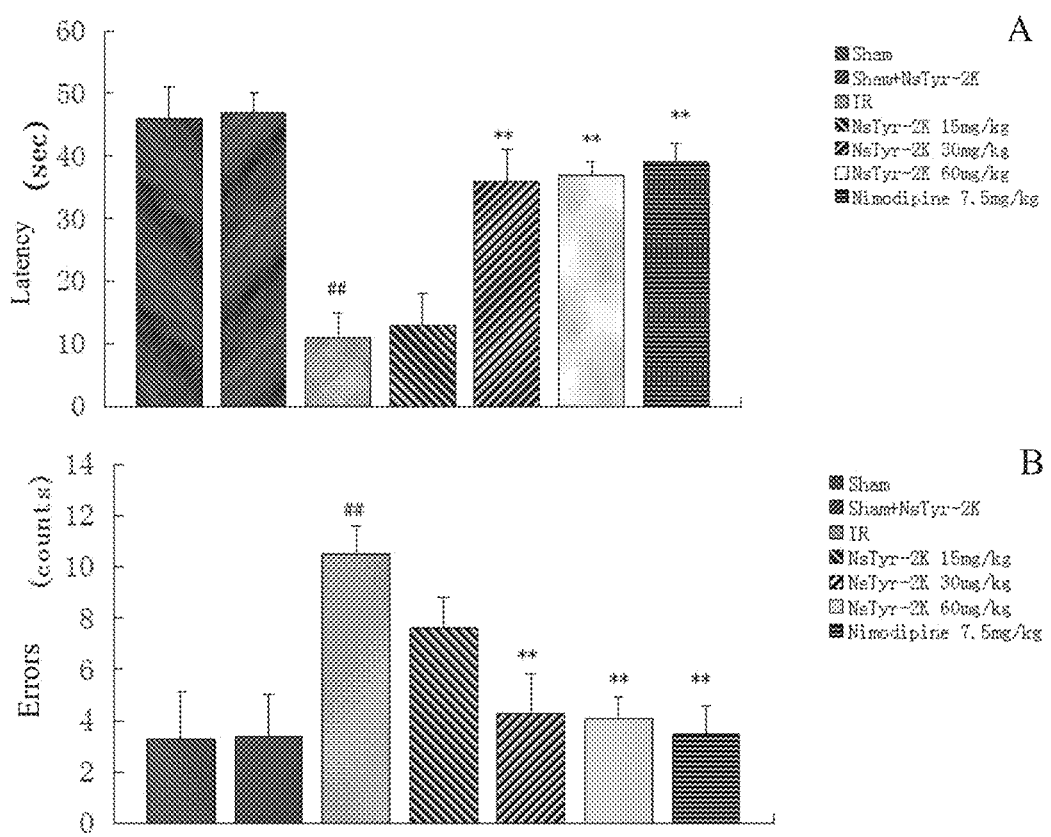
FIG. 4 shows the effects of NsTyr-2K on animals with cerebral ischemia during latency (FIG. 4A) in dark avoidance test in Embodiment 5 of the present invention and error counts within 5 min (FIG. 4B)

Dark avoidance test was used to evaluate the effects of NsTyr-2K influence on animal learning and memory abilities. Results are shown in FIG. 4. Significantly, when compared with the sham operation group (normal), the group of gerbils with ischemia had an increased error counts within 5 min, and a shortened latency. However, when compared with the ischemia group, three-dose groups with 15, 30, 60 mg/kg of NsTyr-2K and the nimotop control group (positive) showed much fewer error counts within 5 min (FIG. 4B) and a much prolonged latency (FIG. 4A).

3. Morris Water Maze Test

Figure 5:
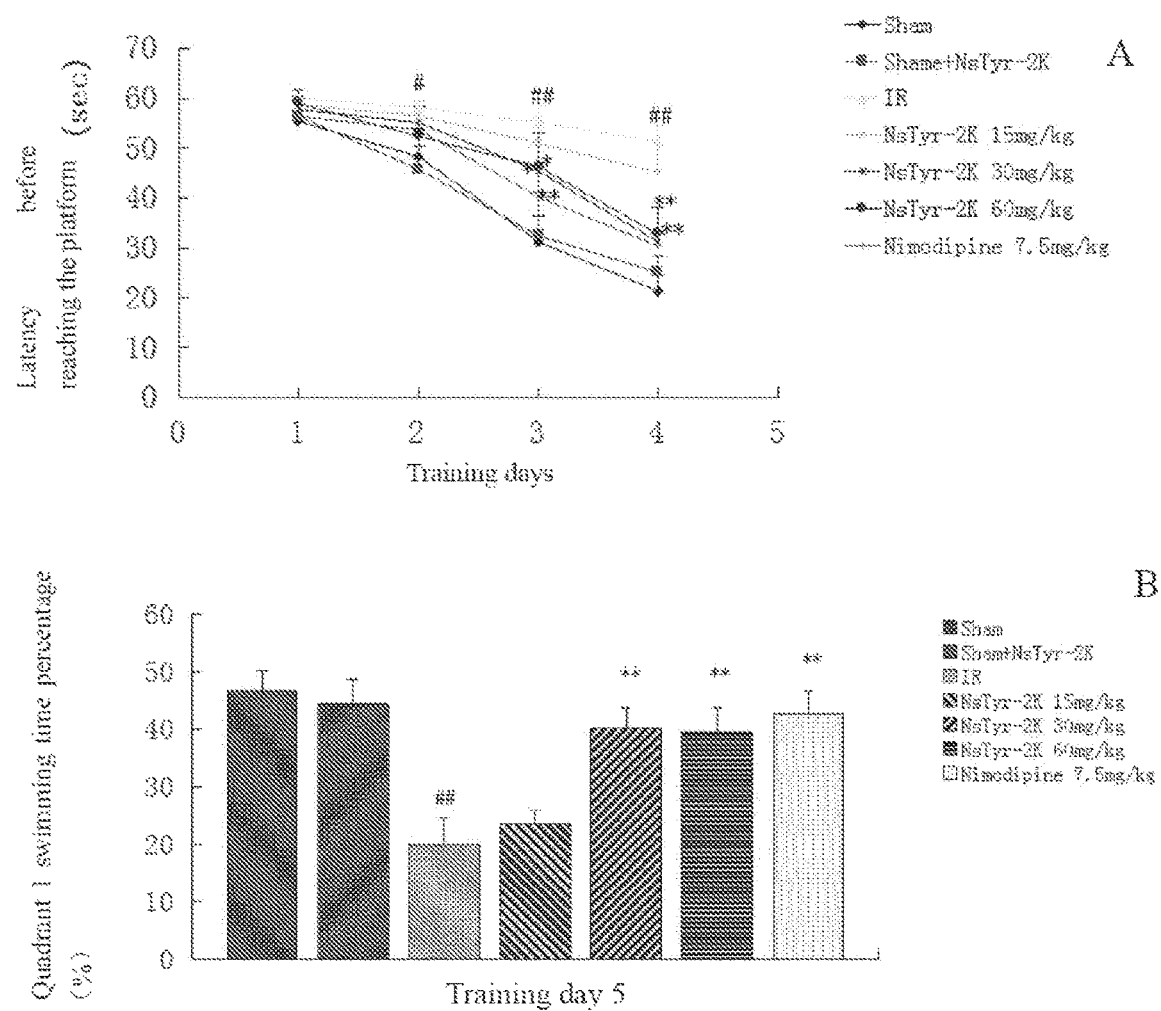
FIG. 5 shows the effects of NsTyr-2K on gerbils with cerebral ischemia during latency (FIG. 5A) in Morris water maze test in Embodiment 5 of the invention and the first quadrant swimming time percentage (FIG. 5B)

Results are shown in FIG. 5. On training day 1, normal gerbils had a latency of 56.3+/−7.42 s before reaching the platform, and a swimming distance of 6,030.1+/−711.73 cm. As training sessions increased gerbils showed an ongoing decline in latency and swimming distance by learning and remembering the position of underwater platform. Up to day 4, for normal animals their latency fell to 29.8+/−12.55 s, and their swimming distance to 3,216.5+/−1,026.46 cm. From day 1 to day 2, there was no evident difference in the average latency before reaching the platform and the swimming distance prior to going onto the platform between the ischemia group of gerbils and any of the other groups. As training sessions increased, the latency and swimming distance of each group of gerbils before reaching the platform was shortened. The gap between the ischemia group and any of the other groups began to widen and reached the record on day 4. Compared with the ischemia group, the two groups respectively with 30 and 60 mg/kg of NsTyr-2K and the nimotop control group (positive) showed evidently, on days 3 and 4, a shortened period before finding the underwater platform and a shortened swimming distance, which is of statistical significance, while there was no obvious difference between the treatment group with 15 mg/kg NsTyr-2K and the model group (FIG. 6A). On day 5, when the platform was removed on a probe test, the ischemia group showed evidently a lower time percentage and a lower swimming distance percentage in the first quadrant within which the platform was located than the sham operation group (the normal group) and the treatment groups with 30 and 60 mg/kg of NsTyr-2K and the nimotop control group (FIG. 5B), which is of statistical difference (P<0.05).

EXAMPLE 6

The Effects of N-Stearoyl Amino Acid Salt on Neurobehavioral Disorder Caused by Senile Dementia and Parkinson's Disease 1. Test Materials Materials for open-field test: a spontaneous activity watch box (80×80×30), on top of which is furnished with a fluorescent lamp as a lighting system, and on the center of whose roof is a CCD camera connected to the computer; and an ethological computer image analysis system (SHANGHAI MOBILEDATUM TECH INFORMATION CO. LTD).

Materials for high plus maze: consisting of two opening arms opposite to each other and two closing arms opposite to each other, a central platform connecting the aforesaid arms, and a short, 1-cm-high damper along the edges of the opening arms (to prevent animals from slipping off the maze in the process of exploring), with the floors of the four arms and the central platform being black; the floor of the maze adjusted to be 50 cm away from the laboratory ground; and an ethological computer image analysis system (SHANGHAI MOBILEDATUM TECH INFORMATION CO. LTD).

Materials for rota rod test: rotary rod type fatigue tester YLS-4C (SHANGHAI MOBILEDATUM TECH INFORMATION CO. LTD).

Materials for water maze test: a constant-temperature swimming pool, a platform for mice, and an ethological computer image analysis system (SHANGHAI MOBILEDATUM TECH INFORMATION CO. LTD).

Laboratory animals: C57BL/6I (from Jackson Lab) (APP/PS1/TAU transgenic mice) in C57BL/6J (TAU transgenic mice). All APP/PS1/TAU transgenic mice and TAU transgenic mice belong to the mouse disease model as for Alzheimer's disease.

NsTyr-2Na (synthesized by our Teaching and Research Section).

2. For Test Methods the Following Three Articles were Referred to:

[1] Priscila Cagni, Mrilia Barros. Cannabinoid type I receptor ligands WIN 55,212-2 and AM251 alter anxiety-like behaviors of marmoset monkeys in an open-field test. Behavioural Brain Research 2013; 240:91-94.

[2] Filali M, Lalonde R, Theriault P, Julien C, Calon F. Planel E. Cognitive an non-cognitive behaviors in the triple transgenic mouse model of Alzheimer's disease expressing mutated APP. PS1, and Mapt (3×Tg-AD). Behavioural Brain Research 2012; 234:334-342.

[3] John C S, Currie P J. N-Arachidonoyl-serotonin in the basolateral amygdale increases anxiolytic behavior in the high plus maze. Behavioural Brain Research 2012:233:382-388.

3. Test Results 3.1 Open-Field Test

Principles: Open-field test is useful for evaluation of mouse anxiety and behavior probing the outside world. By nature mice are capable of both exploring the unknown territory and protecting themselves from damage due to external potential risks. Open-field test, therefore, can test such mouse capabilities by recording their duration of stay at the marginal area and the central area (where anxiety occurs) in an open field. Meanwhile, the test as such can also measure mouse movement capabilities such as speed.

Figure 6:
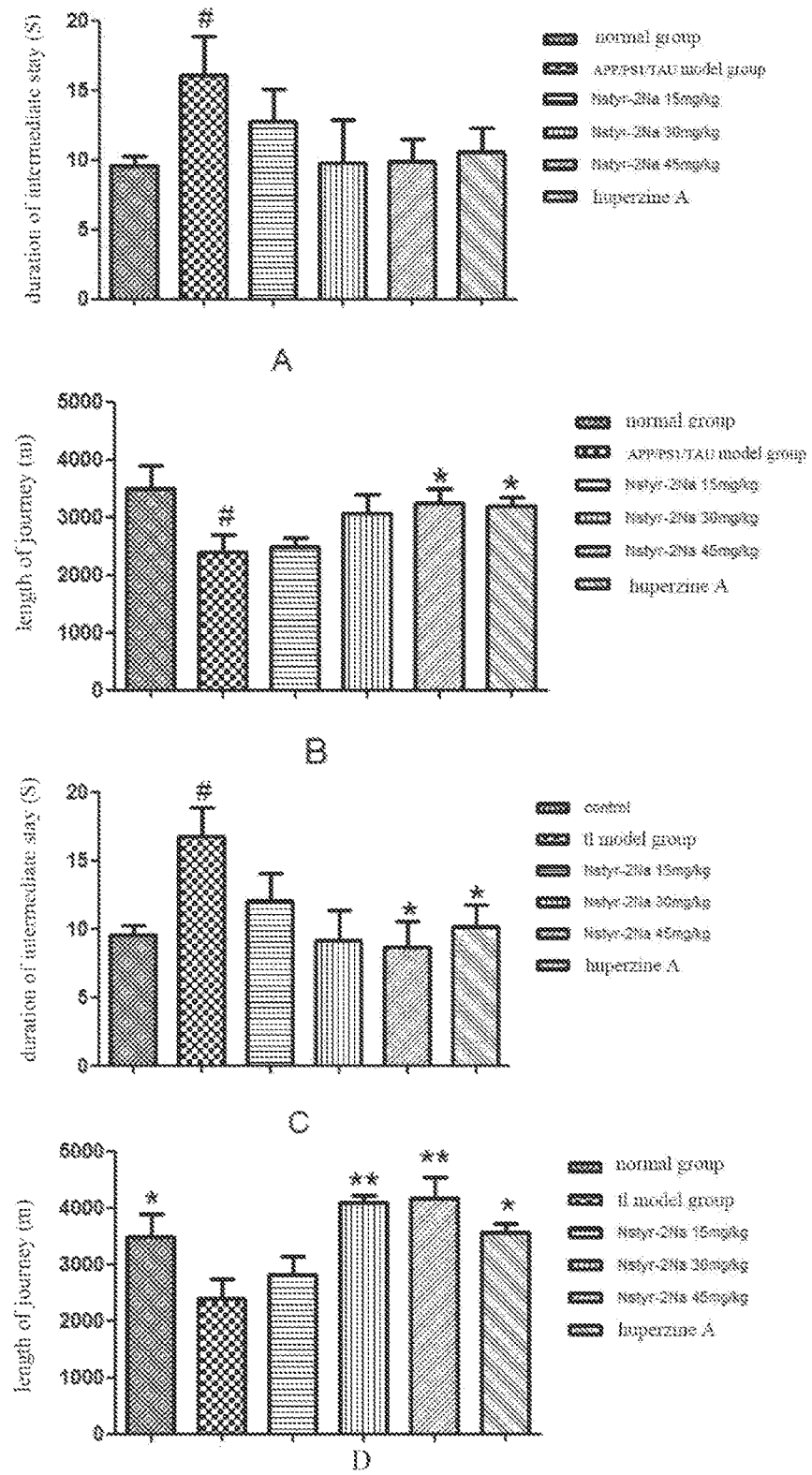
FIG. 6 shows the results of open-field test in Embodiment 6 of the present invention.

Test results are shown in FIG. 6: FIGS. 6A, B show that APP/PS1/TAU transgenic mice displayed evident difference respectively in the central activity area and in the journey during the test. Given different doses of NsTyr-2Na (low-dose: 15 mg/kg; medium-dose: 30 mg/kg; high-dose: 45 mg/kg), the duration of stay at the central activity area could not be changed, and high-dose could increase mouse journey. This shows that NsTyr-2Na can promote transgenic mouse activity, but cannot change their low-anxiety status. FIG. 5A shows temporal difference caused by different doses administered to APP/PS1/TAU transgenic mice. In FIG. 6A, Control: the normal group; Apptl model: APP/PS1/TAU transgenic mice; low: low-dose group (15 mg/kg); medium: medium-dose group (30 mg/kg); high: high-dose group (45 mg/kg); Y: the positive group, huperzine A; the same seen in the following FIGS. 6B-D. FIG. 5A shows that there was difference between the model and the normal group; and that the dosing group had a trend as such but produced no difference. FIG. 6B shows the changing journey of APP/PS1/TAU transgenic mice; in FIG. 6B, there was difference between the model and the normal group; and high-dose administration improved mouse movement capability.

FIGS. 6C and D show that there was significant difference in movement capability during open-field test and the duration of stay in the central area between the group of TAU transgenic mice and the normal group. Medium-dose and high-dose administration could enhance transgenic mouse movement ability, and reduce their duration of stay in the central area and change their low-anxiety status at the same time. FIG. 6C indicates the change of athletic time in the central area for TAU transgenic mice, which tended to be prolonged for the transgenic animal model, meaning that they were in low anxiety state, and that high-dose administration can lessen anxiety. FIG. 6D indicates the change of TAU transgenic mouse journey, which shows the transgenic animal model group had a significantly lower activity, and that both medium- and high-dose administration could enhance autonomic activity.

In FIG. 6, the "#" means P<0.05 when compared with the normal group; the "*" means P<0.05 when compared with the animal model group; the "**" means P<0.01 when compared with the animal model group).

3.2 High Plus Maze Test

Principles: With a couple of opening arms and another couple of closing arms, the high plus maze is useful for assessment of animal anxiety by taking advantage of animal tendency to explore a new extraneous environment as well as their fear of high and open extending arms, which form a behavioral conflict. Rodents tend to move within closing arms due to their fondness of dark, but will, out of curiosity, go into opening arms and move around there. When stimulated by a novel environment, they will engender an impulse to explore and a fear at the same time. Hence a psychological conflict and a sense of anxiety as well.

Figure 7:
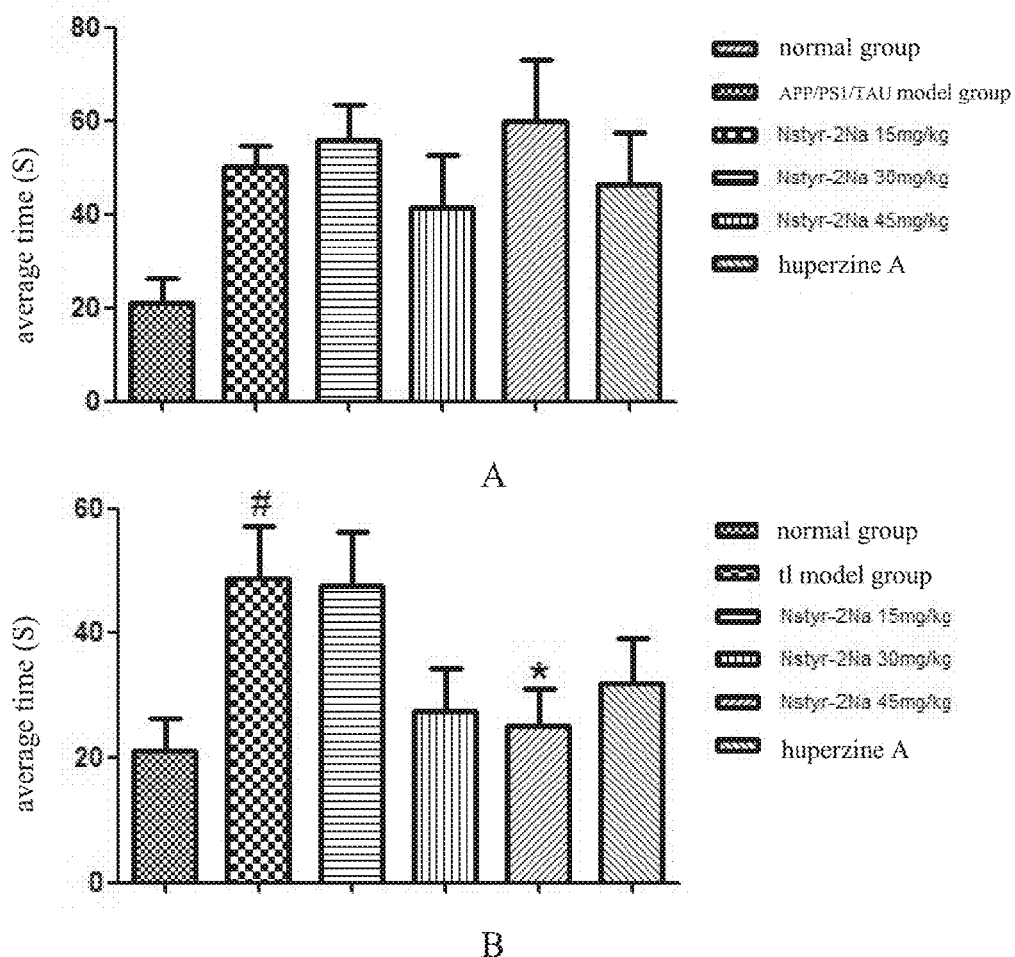
FIG. 7 shows the results of high plus maze test in Embodiment 6 of the present invention.

Test results are shown in FIG. 7: FIG. 7A shows that APP/PS1/TAU transgenic mice developed low anxiety, which different doses of NsTyr-2Na did not change, though medium-dose group had such a trend. FIG. 7B shows that compared with the normal group, the TAU transgenic mouse group built low anxiety, and showed a significant difference. At the same time, when administered with different doses of NsTyr-2Na, the low-anxiety state was changed. High-dose administration had a significant difference. In FIG. 7 the "#" means P<0.05 when compared with the normal group; the "*" means P<0.05 when compared with the animal model group.

3.3 Rota Rod Test

Principles: Rota rod is useful for studying the effects of drugs upon movement coordination and fatigue resistance.

Figure 8:
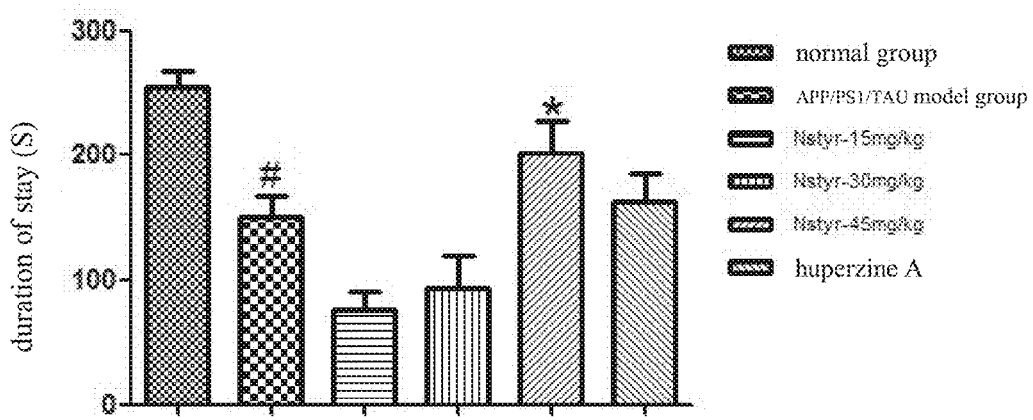
FIG. 8 shows the results of rota rod test in Embodiment 6 of the present invention.

As shown in FIG. 8, test results show that APP/PS1 TAU transgenic mouse movement coordination decreased obviously. Of different doses of NsTyr-2Na administered, high-dose could obviously improve the phenomenon. In FIG. 8, the "#" means P<0.05 when compared with the normal group; the "*" means P<0.05 when compared with the animal model.

3.4 Water Maze Test

Principles: Morris water maze test programs comprise two parts: place navigation test and spatial probe test. The former lasted a few days; each day mice were respectively put into water from four entries several times, and the time they spent seeking the platform hidden underwater (escape latency) was recorded. When place navigation test ended, the platform was removed. The latter recorded the mouse swimming trajectory after the mice were put into water from any chosen entry, and assessed their previous memory of the platform.

Figure 9:
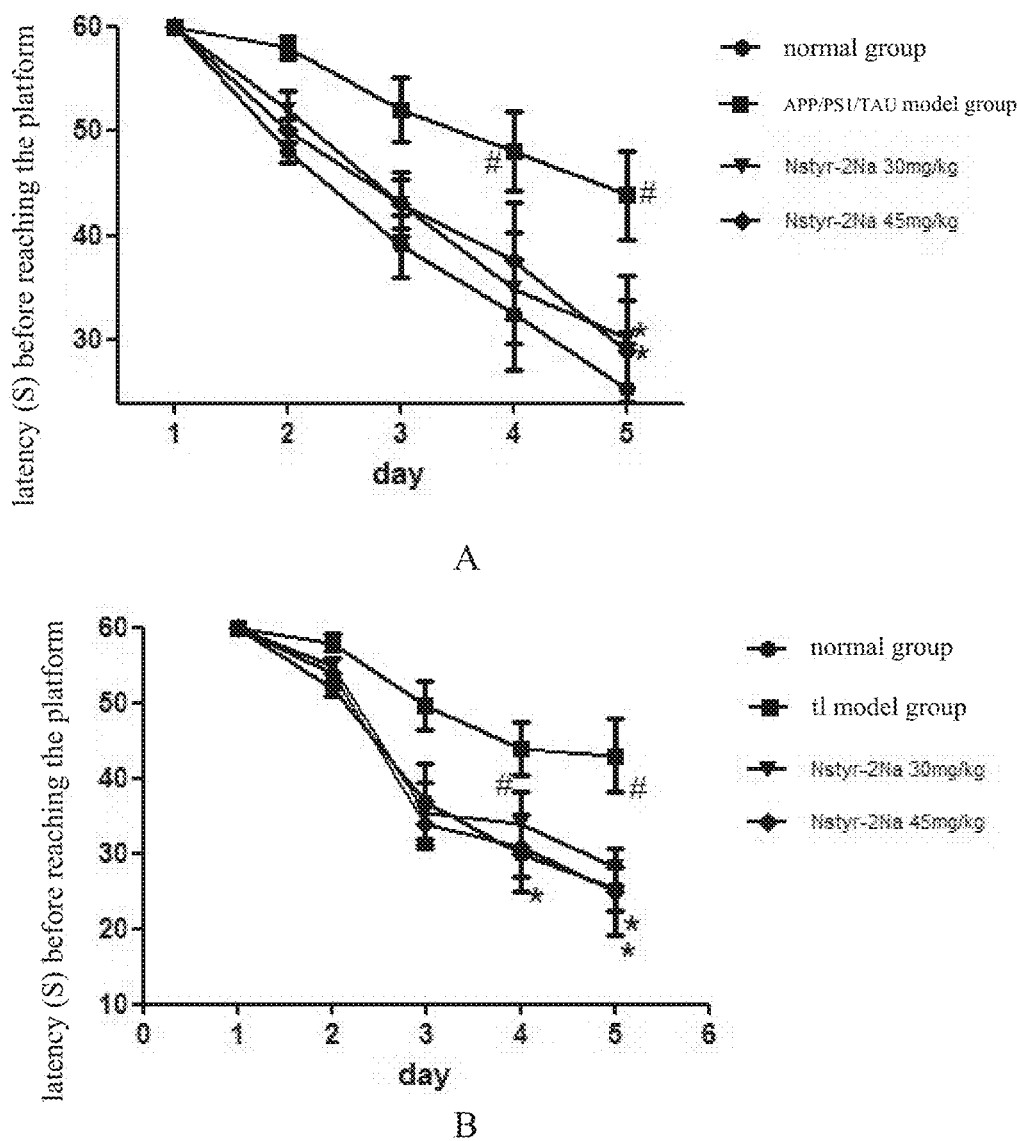
FIG. 9 shows the effects of NsTyr-2Na on transgenic mice in treating learning and memory disorders in Morris water maze test in Embodiment 6 of the present invention.
Figure 10:
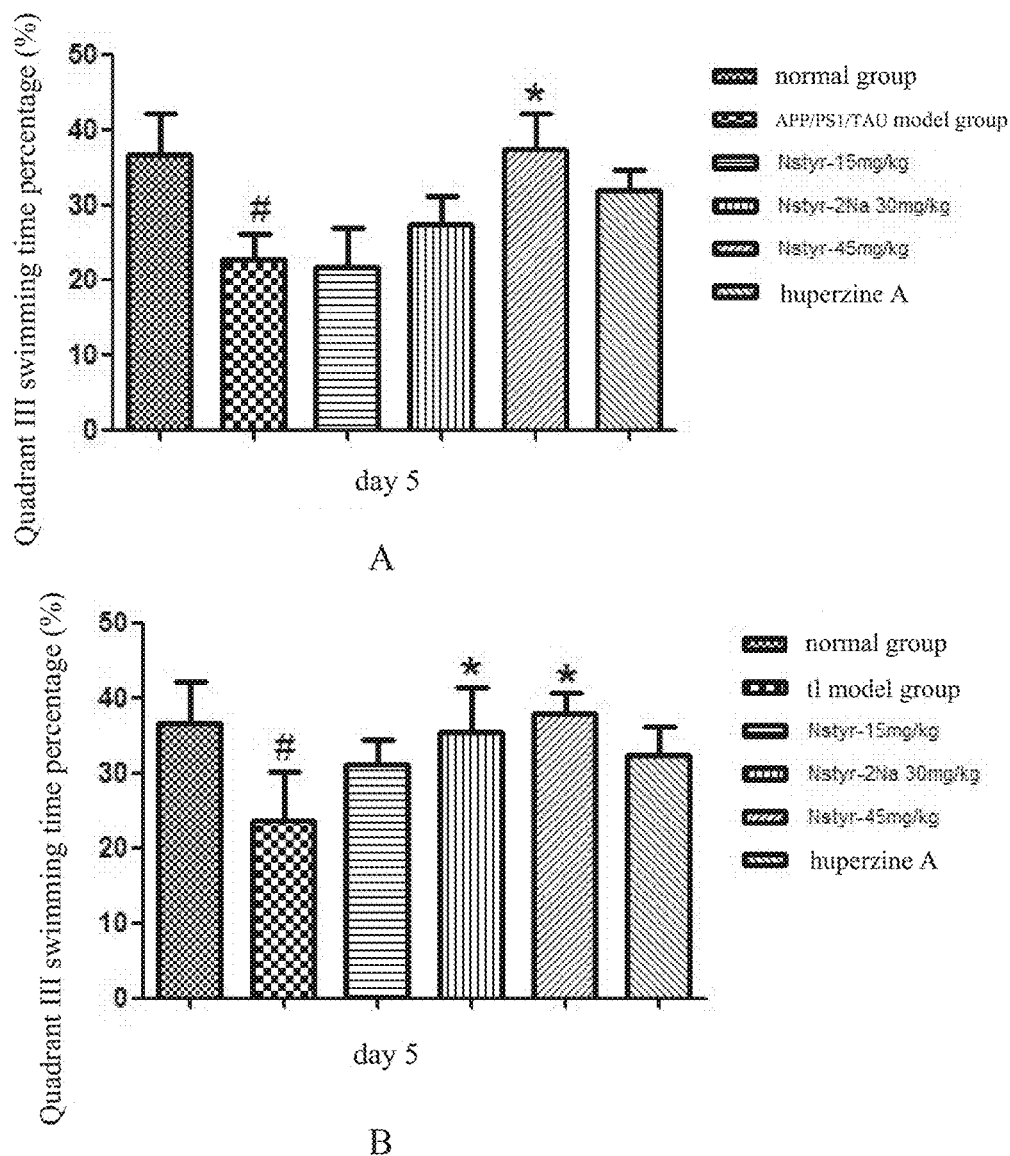
FIG. 10 shows the effects of NsTyr-2Na on transgenic mice in behavioral improvement in Morris water maze test in Embodiment 6 of the present invention.
Figure 11:
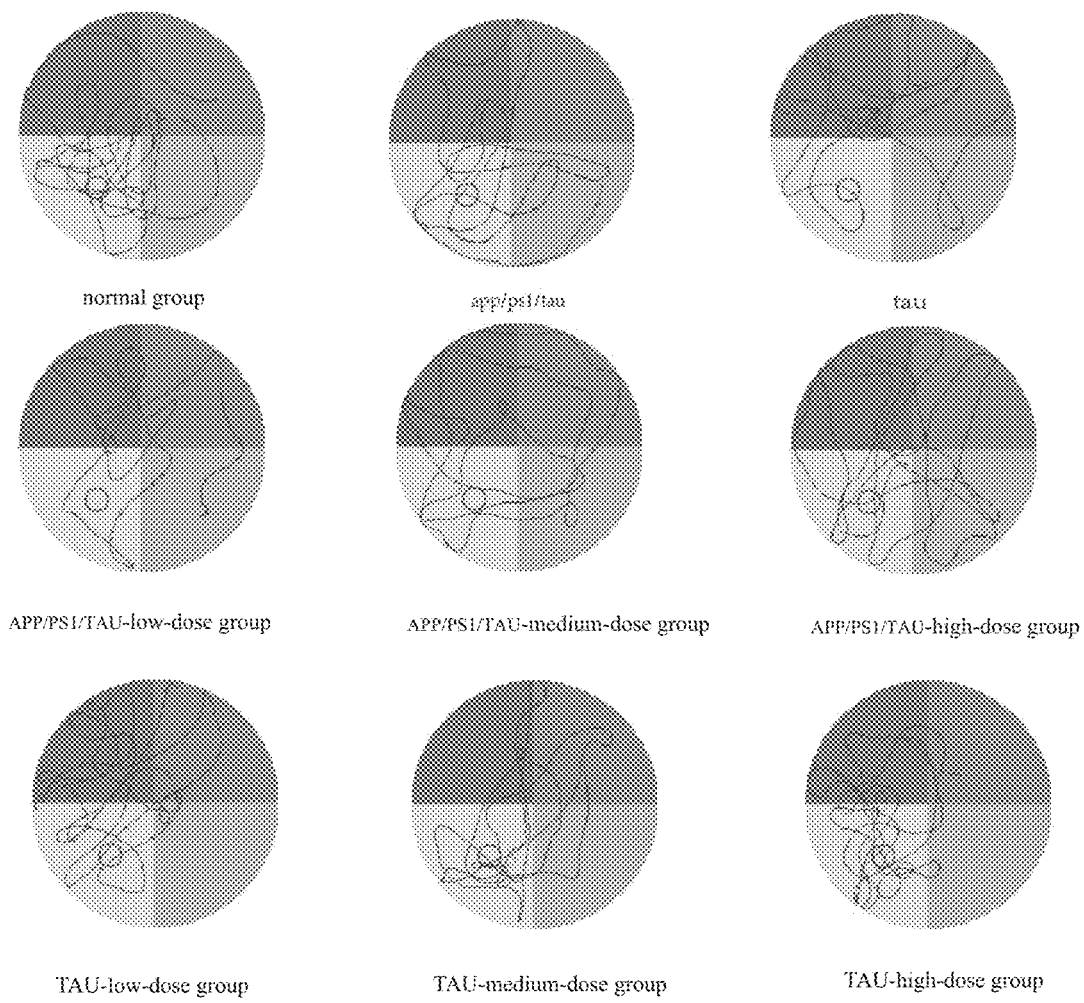
FIG. 11 shows the effects of NsTyr-2Na on transgenic mice in swimming trajectory in Morris water maze spatial probe test in Embodiment 6 of the present invention.

Test results are shown in FIGS. 9, 10 and 11:

FIG. 9 shows that as training sessions increased in place navigation test, mouse latency before reaching the platform and their swimming distance became shorter and shorter by learning and remembering the position of the platform underwater. FIG. 9 shows that among APP/PS1/TAU three groups of transgenic mice, on day 4, the model group showed significant difference #P<0.05, when compared with the normal group, but on the same day there was no significant difference between the dosing group and the model group. On day 5, the medium-dose group and the high-dose group showed significant difference *P<0.05, meaning that NsTyr-2Na could prevent senile dementia to some degree and promote mouse learning and memory, and that dependency on certain dosage appeared as well. FIG. 9B shows that among TAU mono-transgenic mice, the model group showed significant difference #P<0.05 on day 4, when compared with the normal group. Likewise, on day 4 the high-dose group and the model group showed significant difference. On day 5, both the medium-dose group and the high-dose group showed significant difference *P<0.05, indicating that NsTyr-2Na could prevent senile dementia to some degree and promote mouse learning and memory, and that dependency on certain dosage appeared as well. Meanwhile, since triple-transgenic mice feature aggravated dementia due to availability of three genotypes at the same time, NsTyr-2Na can benefit mono-transgenic mice even more with learning and memory.

FIG. 10 shows that in the probe test when the platform was removed on day 5. APP/PS1/TAU triple-transgenic mice indicated significantly lower swimming time percentage (in the third quadrant) than those in the normal group; and the high-dose group showed statistical significance in that aspect. The TAU mono-transgenic mice had a significantly lower swimming time percentage (in the third quadrant) than those in the normal group; the medium-dose group and the high-dose group showed statistical significance, meaning that NsTyr-2Na can help them with spatial probe to a certain extent. Meanwhile, the mono-transgenic model had a better recovery than triple-transgenic mice, which were in agreement with data in place navigation test.

As shown in FIG. 11 and in the transgenic mouse spatial probe test, the normal group had more platform crossings than the model group, a longer duration of stay in the third quadrant, and a longer moving journey. Among APP/PS1/TAU triple-transgenic mice, only the high-dose group could enhance their spatial probing. Of mono-transgenic mice, however, both the medium- and high-dose groups could improve their spatial probing, which was in agreement with data in FIGS. 9 and 10.

Conclusion:

The Alzheimer's disease model mice appeared neurologically dysfunctional in cognition, judgment, thinking, memory. The above tests show that, neurologically, NsTyr-2Na can significantly improve the dysfunctional symptoms of the Alzheimer's disease mice. Moreover, NsTyr-2Na has proved to be able to improve mouse movement in the open-field test and the rota rod test, which suggests that such a role has something to do dopamine pathways. Therefore, the present invention N-stearoyl amino acid salt is of therapeutic significance not only for Alzheimer's disease, but also potentially for Parkinson's disease.

EXAMPLE 7

Acute Toxicity Test

1. Trend of weight change

Figure 12:
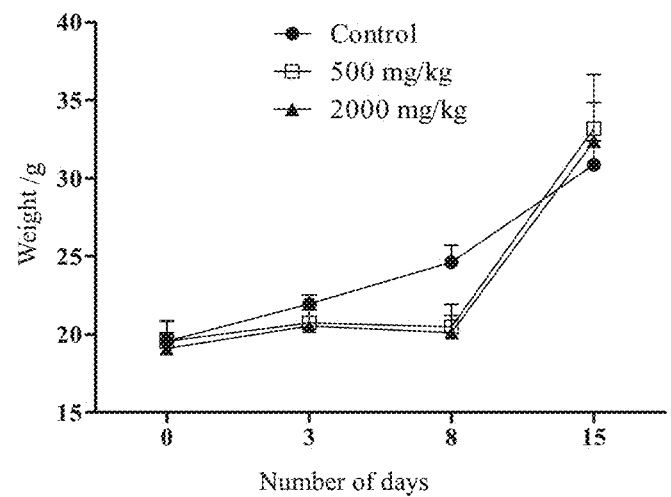
FIG. 12 shows the weight trend of seven mice after oral administration of NsTyr-2K in Embodiment 7 of the present invention.

After oral administration of NsTyr-2K, the mice were weighed. Results are shown in FIG. 12. The control group gained weight steadily during 0-15 days while both the low- and high-dose groups lost weight evidently; and the differential weight between them and the normal group reached the peak up to day 8 since dosing began. However, their weight followed up rapidly as food intake recovered. By the end of the test there was no significant difference among the three groups.

2. Changes of Organ Coefficient

After 15-day administration of NsTyr-2K, the mouse organs (brain, heart, lung, liver and kidney) were studied to see if there was any change.

Figure 13:
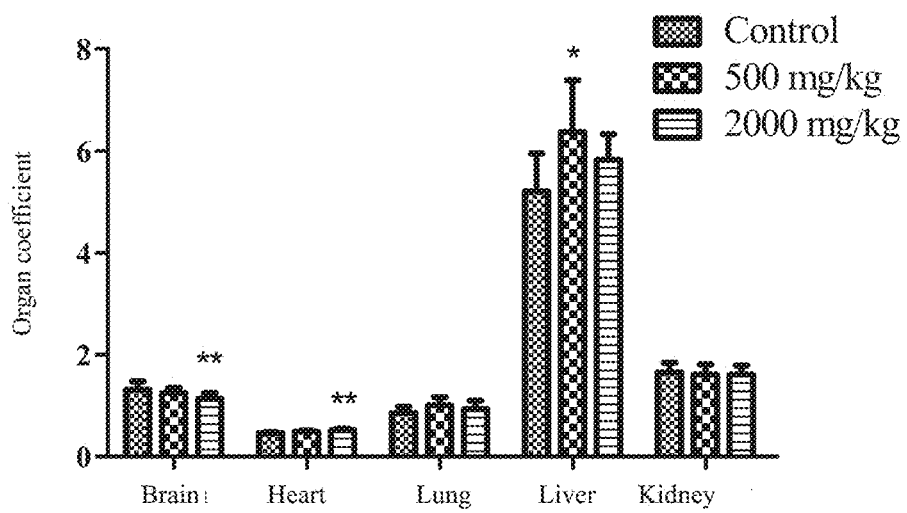
FIG. 13 shows the organ coefficient of seven mice after oral administration of NsTyr-2K in Embodiment 7 of the present invention.

Results of acute toxicity test show that NsTyr-2K had high security, with $LD_{50}>2,000$ mg/kg. The administered group of Kunming mice showed no evidence of behavioral abnormality except loss of appetite and weight after one-week administration; and the weight of the administered group reached the similar level of that of the control group by the end of the test. Research of organ coefficient of suggests that high-dose of NsTyr-2K exerted certain influence upon mouse brain, heart and liver coefficients of (see FIG. 13). However, possibly due to the affinity of NsTyr-2K to the above organs the recipient mice did not show any typical symptoms of the damaged central nervous system such as abnormal convulsion, reflection or movement disorder. This means that mouse brain tissues had not been severely damaged under such dose, and that NsTyr-2K had high safety. Even so, it is necessary to conduct further long-term safety assessment of any possible side effect of NsTyr-2K on liver and hear in the following medicinal research and to precisely determine the amount of administration required.

EXAMPLE 8

N-Stearoyl Amino Acid Salt as a Weight-Reducer

I. Establishment of the Obese Mouse Model

1. Objective: To build an obese mouse model to test the weight-loss activity of stearoyl amino acid salt 2. Method: 60 C57BL/6 mice (aged 3 weeks, male, with a weight of 8.3 g each) were adaptively fed with 12% kcal normal diet for one week, and randomly divided into 6 groups, each consisting of 10 mice. One group (ND) continued to be fed with normal diet, the rest five groups (HFD I~V) were fed with 45% kcal high-fat diet. Every week, the average weight and food intake of each group were recorded until significant difference formed between the two different kinds of groups, while no significant difference formed among the five high-fat diet groups themselves, and if such a status remained for three weeks, the built model would be deemed to be successful.

In the whole test process the mice kept raised in the following environment: temperature: 23±3° C.; humidity: 50±5%; bright and dim alternating cycle: 12 h/12 h; freely available to diet and drinking water in the whole process.

Figure 14:
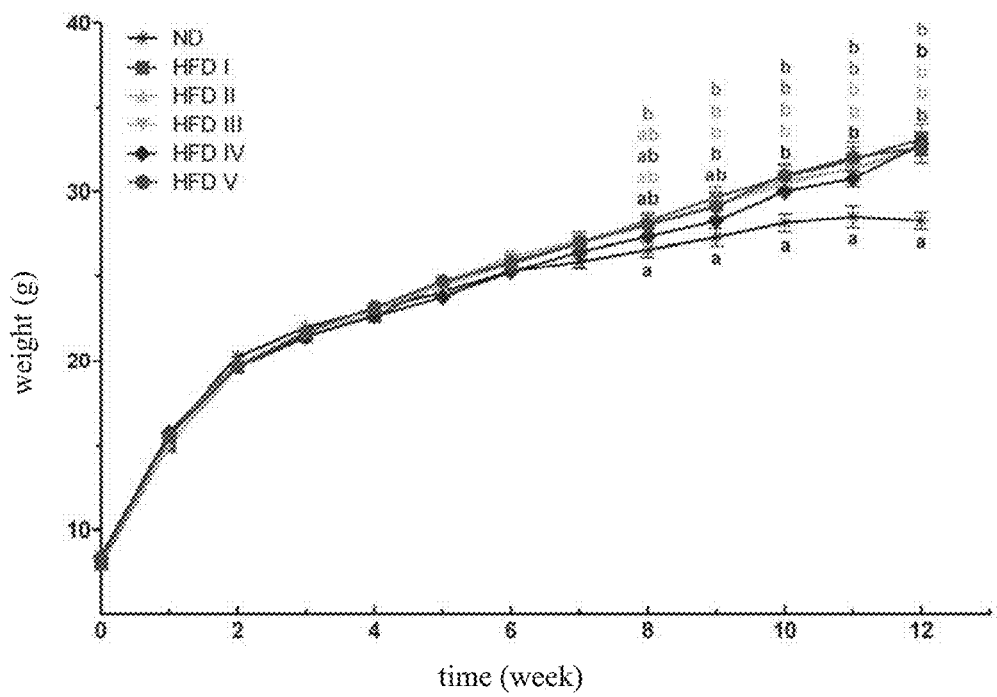
FIG. 14 shows the changing weight of individual groups of mice during 11-week diet intervention in Embodiment 8 of the present invention.

3. Results:

1) As shown in FIG. 14, after being fed with different diets up week 9 (in FIG. 14, the abscissa has 10 positions because stage 0~1 was for adaptive feeding, while all the six groups were fed with the same standard diet, and in the ongoing stages starting from position 1 they began to be fed with different diets), the five high-fat diet groups (HFD I~V) had a significantly higher weight than the normal diet group (ND), and at the same time there was no significant weight difference among the five high-fat diet groups (HFD I~V) themselves. After this weight difference remained 3 weeks, the obesity model eventually became successful (different diets were fed for 11 weeks), when the average weight of the normal diet group (ND) was approximately 28.3 g, and that of the five high-fat diet groups (HFD I~V) was approximately 32.8 g. In FIG. 14, all numerical values were expressed in the form of the average±standard error, n=10, and use of different letters meant that there was significant difference between them (P<0.05).

Figure 15:
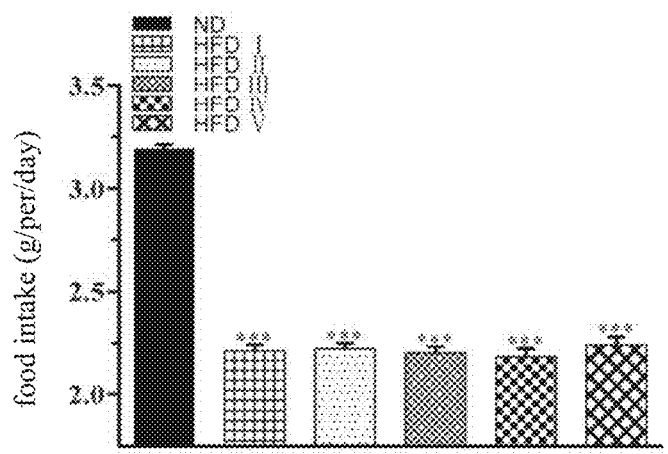
FIG. 15 shows the average food intake histogram of individual groups of mice during 11-week diet intervention in Embodiment 8 of the present invention.

2) As shown in FIG. 15, during 11-week diet intervention (i.e., the period of use of different diets), the average daily intake of the normal diet group (ND) was significantly higher than that of the high-fat diet groups (HFD I~V), but there was no significant difference in the average daily intake among the high-fat diet groups (HFD I~V) themselves. In FIG. 15, all numerical values were expressed in the form of the average±standard error, n=10, and the "***" means significant difference when compared with ND (P<0.001).

4. Conclusion: the obese mouse model is successful, and similar appetite remained among the high-fat diet groups (HFD I~V) in the modeling process.

II. Administration Test

1. Objective: To observe the effects of N-stearoyl amino acid salt (in this example to N-two potassium stearoyl tyrosine, NST-2K, for example) on the obese mouse weight and compare with positive drug Orlistat.

2. Method: ND and HFD I were respectively taken as normal and high-fat diet blank control groups, and were treated with 0.5% sodium carboxymethyl cellulose solution (5 ml/kg/day); HFD II~IV were taken as groups of recipients, and were treated with NST-2K (20, 60, 100 mg/kg/day); HFD V was taken as a positive control group, and treated with Orlistat (100 mg/kg/day). All the above drugs dissolved in aqueous solution of 0.5% sodium carboxymethyl cellulose and were administered. The administration remained four weeks. In each week average weight and food intake were kept in record until the phase of administration ended.

Figure 16:
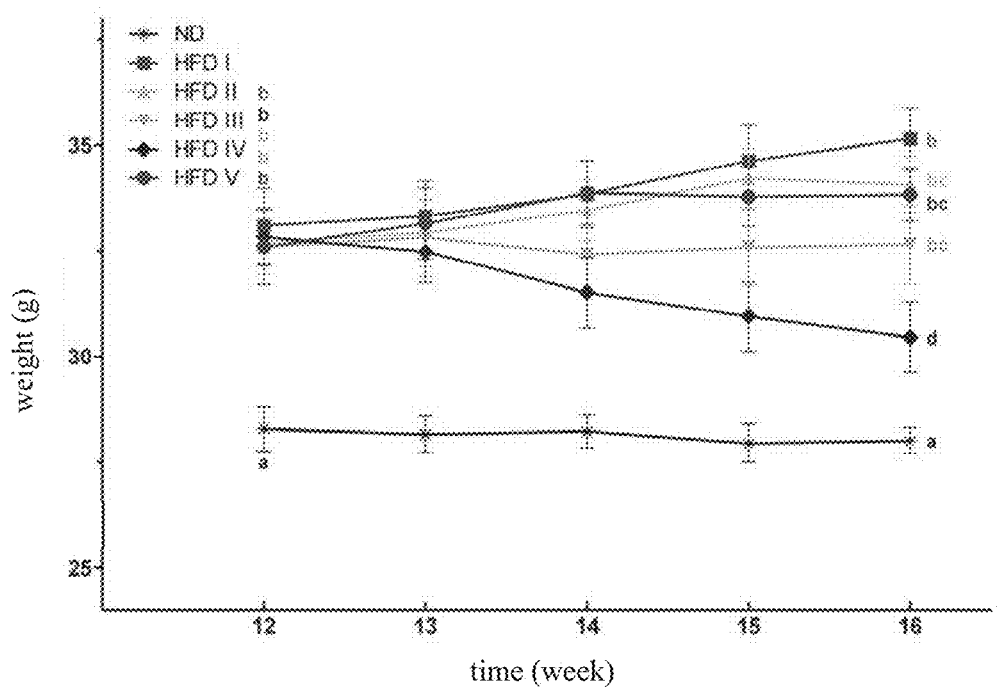
FIG. 16 shows the changing weight of individual groups of mice during four weeks of dosing treatment in Embodiment 8 of the present invention.

3. Results:

1) As shown in FIG. 16, the obese groups HFD II, HFD III and HFD V gained weight more slowly than the blank obesity group HFD I during the phase of administration. However, no significant difference occurred among the above four groups until the end of the administration phase. The weight of the administered obese group HFD IV remained a declining trend as administration time prolonged, and became significantly lower than that of HFD I at the end of administration. In FIG. 16, all numerical values were expressed in the form of the average±standard error, n=10, and use of different letters meant that there was significant difference between them (P<0.05).

Figure 17:
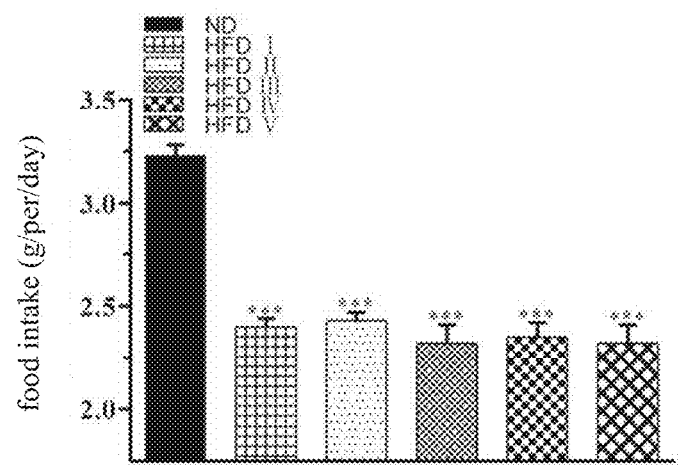
FIG. 17 shows the average food intake histogram of individual groups of mice during four weeks of dosing treatment in Embodiment 8 of the present invention.

2) As shown in FIG. 17, during 4-week administration, the average daily food intake of the normal diet group (ND) was significantly higher than that of the high-fat diet groups (HFD I~V), but no significant difference occurred in daily food intake among the high-fat diet groups (HFD I~V) themselves. In FIG. 4, all numerical values were expressed in the form of the average±standard error, n=10, and the "***" means significant difference when compared with ND (P<0.001).

4. Conclusion:

1) FIG. 16 shows that low- and medium-doses of NST-2K (20, 60 mg/kg/day) and positive drug Orlistat (100 mg/kg/day) can inhibit weight gain in obese mice; high-dose of NST-2K (100 mg/kg/day) can reduce obese mouse weight: with the same dose (100 mg/kg/day), NST-2K has a significantly better weight loss activity than Orlistat.

2) FIG. 17 shows that similar appetite remained among the high-fat diet groups (HFD I~V) during the phase of administration, meaning that neither NST-2K nor Orlistat suppressed appetite to lose weight.

EXAMPLE 9

Collection and Observation of Experimental Animal Fat and Liver Tissues

1. Objective: To observe the abdominal fat content in all the groups, and separate liver and adipose tissues for subsequent H&E staining observation.

2. Method: After administration test in Embodiment 8, the mice were denied food overnight. Their abdominal cavity was opened to observe abdominal fat content in each group of the mice. Epididymal fat, perirenal fat and liver were separated and weighed.

Figure 18:
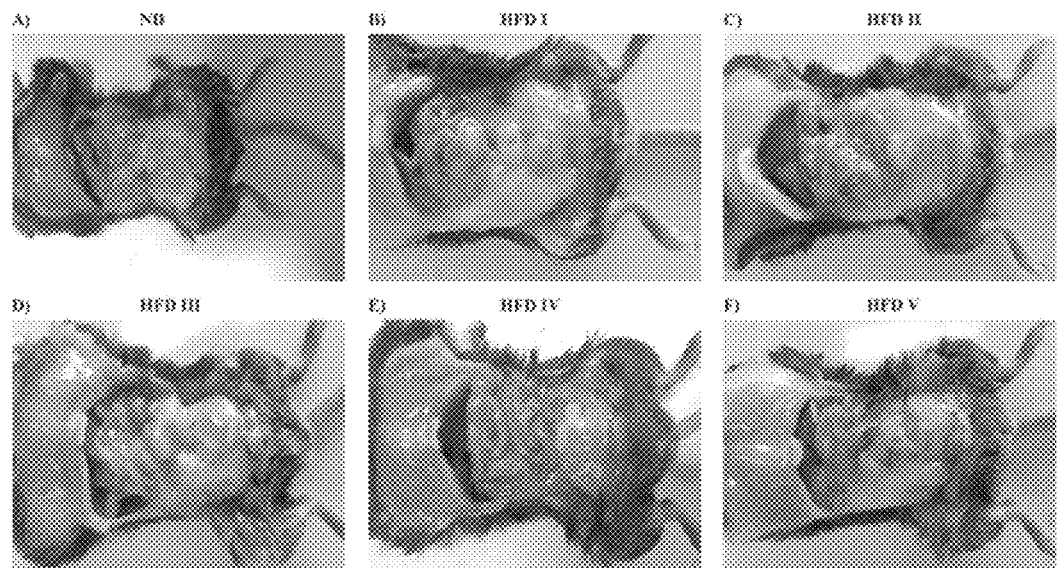
FIG. 18 shows the photograph of mouse abdominal fat in Embodiment 9 of the present invention.

3. Results:

1) FIG. 18 shows that the bodily form and abdominal fat pad of the normal diet group (ND) were significantly smaller than those of the high-fat diet groups (HFD I~V). As doses of NST-2K increased (HFD II~IV), the abdominal fat pad showed a shrinking trend when compared with the blank obesity group (HFD I), wherein HFD IV (the high-dose NST-2K group) showed the most obvious effect, superior to HFD V (the Orlistat group).

2) As shown in Table 4, liver percentage quality showed no significant difference among the high fat-diet groups (HFD I~V), but significantly lower than that of the normal diet group (ND); the epididymal and perirenal fat percentage quality of HFD III and HFD IV and HFD V was significantly lower than that of the blank obesity group (HFD I); and there was no significant difference in epididymal and perirenal fat percentage quality between HFD II (the low-dose NST-2K group) and HFD I.

TABLE 4

Mice liver and adipose tissue percentage quality [a]

| Tissue (g/100 g weight) | ND | HFD I | HFD II | HFD III | HFD IV | HFD V |
|---|---|---|---|---|---|---|
| Liver | 3.80 ± 0.04 | 3.51 ± 0.07** | 3.47 ± 0.05*** | 3.41 ± 0.06*** | 3.46 ± 0.07*** | 3.48 ± 0.06*** |
| Epididymal fat | 1.04 ± 0.06 | 2.99 ± 0.08*** | 2.94 ± 0.11*** | 2.72 ± 0.07***# | 2.64 ± 0.08***## | 2.66 ± 0.07***## |
| perirenal fat | 0.31 ± 0.05 | 1.63 ± 0.10*** | 1.51 ± 0.07*** | 1.37 ± 0.04***## | 1.26 ± 0.05***### | 1.32 ± 0.06***### |

[a] All numerical values were expressed in the form of the average ± standard error, n = 10.
The "" and "*" respectively means significant difference ($P < 0.01$, $P < 0.001$) when compared with ND.
The "#", "##" and "###" $P < 0.001$ respectively mean significant difference ($P < 0.05$, $P < 0.01$, $P < 0.001$) when compared with HFD I.
ND, normal diet blank control group; HFD I, high-fat diet blank control group; HFD II, low-doses NST-2K group (20 mg/kg/day); HFD III, medium-dose NST-2K group (60 mg/kg/day); HFD IV, high-dose NST-2K group (100 mg/kg/day); HFD V, positive control group (100 mg/kg/day Orlistat).

4. Conclusion: NST-2K can reduce abdominal fat quality of obese mice, producing no significant effects on liver quality. With the same dose (100 mg/kg), NST-2K has better effects in reducing abdominal fat quality than Orlistat.

EXAMPLE 10

H&E Staining to Observe Fat and Liver Tissue Morphology

1. Objective: To microscopically observe fat and liver tissue morphology.

2. Method: Epididymal fat and liver were fixed in 10% neutral formaldehyde solution for 48 h. After paraffin embedding they were made into 5 min of slices, and stained with hematoxylin-eosin (H&E staining). Light microscope was used to observe the size of fat cells, the structure of liver cells and adipose accumulation.

Figure 19:
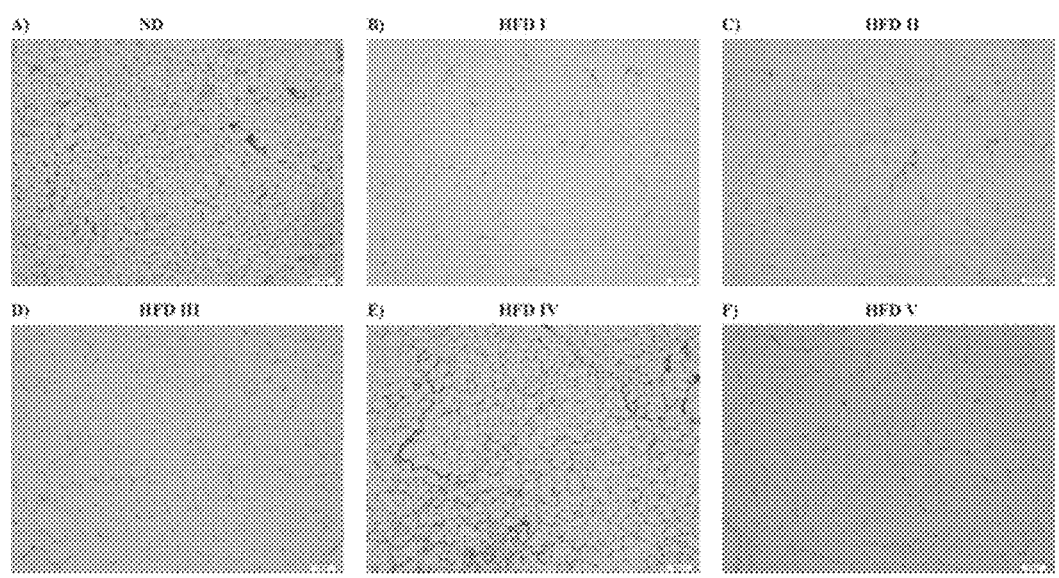
FIG. 19 shows the H&E staining microscopic photos of epididymal adipose tissue slices (scale=100 μm) in Embodiment 10 of the present invention.
Figure 20:
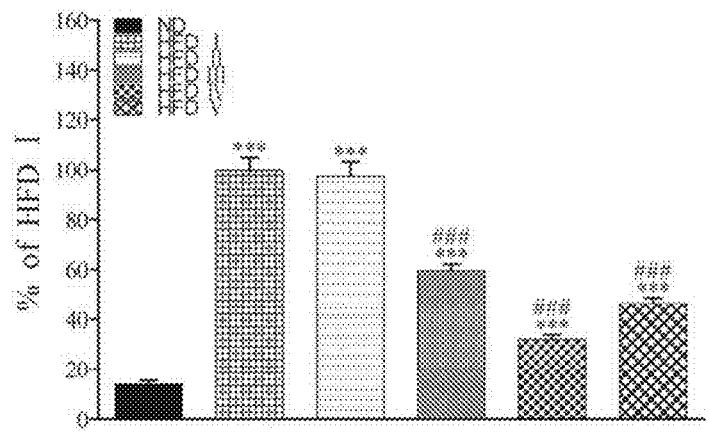
FIG. 20 shows the histogram of the size of epididymal tissue fat cells in Embodiment 10 of the present invention.

3. Results:

1) As shown in FIGS. 19 and 20, HFD I fat cells were significantly greater than ND ones, and the administered groups HFD III and HFD IV and HFD V had evidently smaller fat cells than HFD I; and treatment of low-dose NST-2K (HFD II) could not significantly shrink fat cells. In FIG. 20, all numerical values were expressed in the form of the average±standard error, n=10. The "***" means significant difference (P<0.001) when compared with ND; and the "###" means significant difference (P<0.001) when compared with HFD I.

Figure 21:
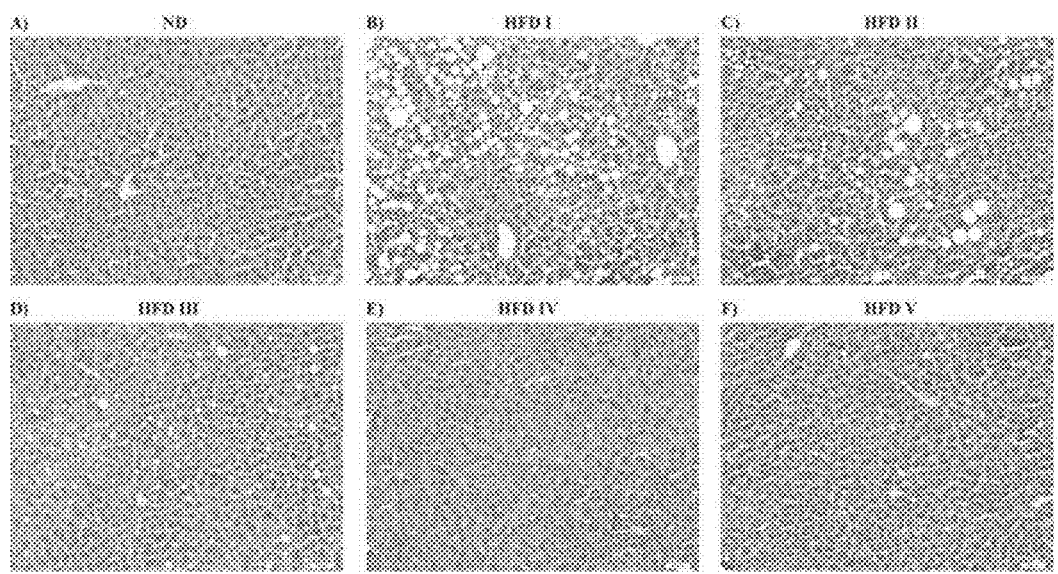
FIG. 21 shows the H&E staining microscopic photos of liver tissue slices in Embodiment 10 of the present invention (scale=50 μm)

2) FIG. 21 shows that there was severe fat accumulation in HFD I liver tissues, and that the accumulation began to ease as the administration dose of NST-2K or Orlistat increased.

4. Conclusion: NST-2K can shrink the size of obese mouse fat cells, and ease obese mouse liver fatty deterioration.

The above embodiments described have expressed only the implement methods of the present invention, whose description, though specific and detailed, is not to be construed to be limiting the scope of the present invention patent. It should be noted that, to those skilled in the art, a number of transformations and advancements of the present invention can be made without breaking away from the conception of the present invention, all of which belong to the scope of protection of the present invention. Therefore, the attached claims herein shall prevail as to the scope of protection of the present invention patent.

The invention claimed is:

1. A method of reducing a body weight of a subject in need thereof or treating a fatty liver in a subject in need thereof, the method comprising administering to the subject a pharmaceutical composition comprising a stearoyl amino acid salt of formula (II) or formula (III), and a pharmaceutically acceptable carrier:

(II)

(III)

wherein M in the formula (II) is a monovalent metal cation or $NH_4^+$; and $M^{2+}$ in the formula (III) is a divalent metal cation.

2. The method according to claim 1, wherein M in the formula (II) is selected from the group consisting of $K^+$, $Na^+$ and $NH_4^+$.

3. The method according to claim 1, wherein $M^{2+}$ in the formula (III) is selected from the group consisting of $Ba^{2+}$, $Ca^{2+}$ and $Mg^{2+}$.

4. A method for preparing a stearoyl amino acid salt of formula (II) or formula (III):

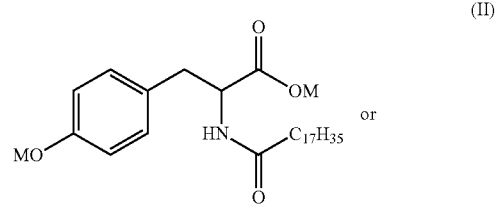

(II)

-continued

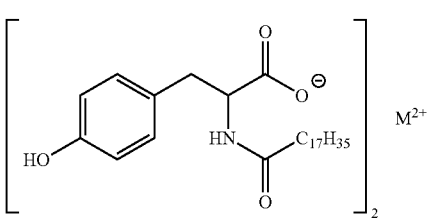
(III)

wherein the method comprises: preparing the stearoyl amino acid salt from an N-stearoyl amino acid methyl ester of formula (VII) through alkaline hydrolysis:

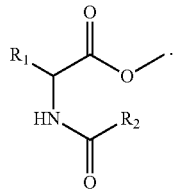
(VII)

wherein the N-stearoyl amino acid methyl ester is prepared by treating a compound of formula (VI) with a compound of formula (V) under alkaline conditions:

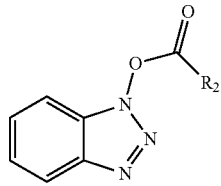
(VI)

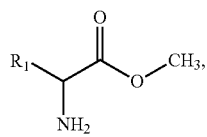
(V)

the compound of formula (VI) is prepared by reacting a compound of formula (IV) with a coupling agent 1-hydroxybenzotriazole:

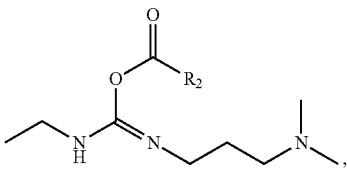
(IV)

and the compound of formula (IV) is prepared by reacting 1-ethyl-(3-dimethyl amino propyl) carbonyl imine hydrochloride, stearic acid and triethylamine with a catalyst 4-dimethyl amino pyridine, wherein $R_2$ is $C_{17}H_{35}$; $R_1$ is —$CH_2$-phenol; M in the formula (II) is a monovalent metal cation or $NH_4^+$; and $M^{2+}$ in the formula (III) is a divalent metal cation.

5. A method of reducing a body weight of a subject in need thereof or treating a fatty liver in a subject in need thereof, the method comprising administering to the subject a pharmaceutical composition comprising a stearoyl amino acid salt of formula (II) or formula (III), and a pharmaceutically acceptable carrier:

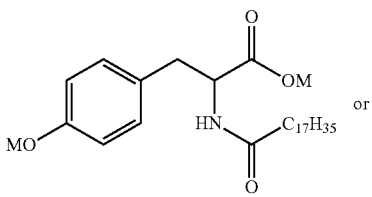
(II)

or

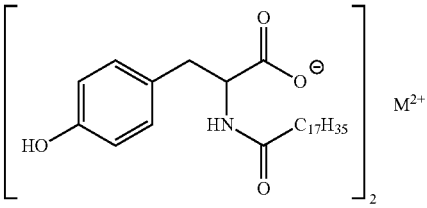
(III)

wherein M in the formula (II) is selected from the group consisting of $K^+$, $Na^+$ and $NH_4^+$;

and $M^{2+}$ in the formula (III) is selected from the group consisting of $Ba^{2+}$, $Ca^{2+}$ and $Mg^{2+}$.

6. The method of claim 1, wherein the method is for reducing the body weight of a subject in need thereof.

7. The method of claim 1, wherein the method is for treating a fatty liver in a subject in need thereof.

8. The method of claim 5, wherein the method is for reducing the body weight of a subject in need thereof.

9. The method of claim 5, wherein the method is for treating a fatty liver in a subject in need thereof.

10. The method of claim 5, wherein the stearoyl amino acid salt has the formula (II), and wherein M in the formula (II) is $K^+$.

* * * * *